US009504453B2

(12) United States Patent
Haberstich et al.

(10) Patent No.: US 9,504,453 B2
(45) Date of Patent: *Nov. 29, 2016

(54) MRI BIOPSY DEVICE

(71) Applicant: Devicor Medical Products, Inc., Cincinnati, OH (US)

(72) Inventors: Wells D. Haberstich, Loveland, OH (US); Raj G. Raghavendran, Mason, OH (US); John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,733

(22) Filed: Jun. 15, 2016

(65) Prior Publication Data

US 2016/0296213 A1 Oct. 13, 2016

Related U.S. Application Data

(63) Continuation of application No. 14/568,478, filed on Dec. 12, 2014, now Pat. No. 9,392,999, which is a (Continued)

(51) Int. Cl.
*A61B 5/00* (2006.01)
*A61B 10/02* (2006.01)
(Continued)

(52) U.S. Cl.
CPC ........... *A61B 10/0275* (2013.01); *A61B 5/055* (2013.01); *A61B 5/065* (2013.01);

(Continued)

(58) Field of Classification Search
CPC .............. A61B 10/02; A61B 10/0233; A61B 10/0266; A61B 10/0275; A61B 10/0283; A61B 10/0041
See application file for complete search history.

(56) References Cited

U.S. PATENT DOCUMENTS

| 873,745 A | 12/1907 | Haynes |
| 1,337,733 A | 4/1920 | Sweetland et al. |

(Continued)

FOREIGN PATENT DOCUMENTS

| AU | 2007202271 A1 | 12/2007 |
| AU | 2012233005 A1 | 10/2012 |

(Continued)

OTHER PUBLICATIONS

Daniel, B.L. et al., "An MRI-Compatible Semiautomated Vacuum-Assisted Breast Biopsy System: Initial Feasibility Study," J. of Magnetic Resonance Imaging, vol. 2 (2005) pp. 637-644.

(Continued)

*Primary Examiner* — Max Hindenburg
(74) *Attorney, Agent, or Firm* — Frost Brown Todd LLC

(57) ABSTRACT

A magnetic resonance imaging (MRI) compatible core biopsy system uses a biopsy device having intuitive graphical displays and a detachable remote keypad that advantageously allows convenient control even within the close confines afforded by a localization fixture installed within a breast coil that localizes a patient's breast and guides a probe of the biopsy device relative to the localized breast. A control module for interactive control and power generation are remotely positioned and communicate and transmit rotational mechanical energy via sheathed cable.

20 Claims, 14 Drawing Sheets

Related U.S. Application Data continuation of application No. 11/419,567, filed on May 22, 2006, now Pat. No. 8,932,233, which is a continuation-in-part of application No. 11/103,959, filed on Apr. 12, 2005, now Pat. No. 7,831,290.

(60) Provisional application No. 60/573,510, filed on May 21, 2004.

(51) Int. Cl.
    *A61B 5/055*     (2006.01)
    *A61B 10/00*     (2006.01)
    *A61B 17/34*     (2006.01)
    *A61B 5/06*     (2006.01)
    *A61B 17/00*     (2006.01)

(52) U.S. Cl.
    CPC ............ *A61B 5/743* (2013.01); *A61B 5/7435* (2013.01); *A61B 10/0041* (2013.01); *A61B 17/3403* (2013.01); *A61B 90/17* (2016.02); *A61B 10/0283* (2013.01); *A61B 2010/0208* (2013.01); *A61B 2017/00911* (2013.01)

(56) References Cited

U.S. PATENT DOCUMENTS

| | | |
|---|---|---|
| 1,693,741 A | 12/1928 | Wuest |
| 1,734,652 A | 11/1929 | Sweetland |
| 1,941,982 A | 1/1934 | Gill |
| 2,047,714 A | 7/1936 | Smith |
| 2,656,930 A | 10/1953 | De Vries |
| 2,689,048 A | 9/1954 | Powers |
| 3,401,684 A | 9/1968 | Dremann |
| 3,456,806 A | 7/1969 | Borston |
| 3,561,429 A | 2/1971 | Jewett et al. |
| 3,732,858 A | 5/1973 | Banko |
| 3,734,099 A | 5/1973 | Bender et al. |
| 3,785,380 A | 1/1974 | Brumfield |
| 3,815,604 A | 6/1974 | O'Malley et al. |
| 3,833,000 A | 9/1974 | Bridgman |
| 3,844,272 A | 10/1974 | Banko |
| 3,889,657 A | 6/1975 | Baumgarten |
| 3,890,712 A | 6/1975 | Lopez |
| 3,937,222 A | 2/1976 | Banko |
| 3,938,505 A | 2/1976 | Jamshidi |
| 3,945,375 A | 3/1976 | Banko |
| 3,994,297 A | 11/1976 | Kopf |
| 3,996,935 A | 12/1976 | Banko |
| 4,007,742 A | 2/1977 | Banko |
| D243,559 S | 3/1977 | Hoyle et al. |
| 4,019,514 A | 4/1977 | Banko |
| 4,030,719 A | 6/1977 | Gabriele et al. |
| 4,083,706 A | 4/1978 | Wiley |
| 4,101,756 A | 7/1978 | Yamano |
| 4,117,843 A | 10/1978 | Banko |
| 4,159,773 A | 7/1979 | Losenno |
| 4,167,943 A | 9/1979 | Banko |
| 4,167,944 A | 9/1979 | Banko |
| 4,169,060 A | 9/1979 | Columbus |
| 4,177,814 A | 12/1979 | Knepshield et al. |
| 4,203,444 A | 5/1980 | Bonnell et al. |
| 4,210,146 A | 7/1980 | Banko |
| 4,221,225 A | 9/1980 | Sloan |
| 4,257,425 A | 3/1981 | Ryan |
| 4,282,098 A | 8/1981 | Morgan, Jr. |
| 4,308,878 A | 1/1982 | Silva |
| 4,316,465 A | 2/1982 | Dotson, Jr. |
| 4,320,761 A | 3/1982 | Haddad |
| 4,354,093 A | 10/1982 | Zago |
| 4,368,734 A | 1/1983 | Banko |
| 4,382,808 A | 5/1983 | Van Wormer, Jr. et al. |
| 4,393,879 A | 7/1983 | Milgrom |
| 4,468,217 A | 8/1984 | Kuzmick et al. |
| 4,513,745 A | 4/1985 | Amoils |
| 4,517,977 A | 5/1985 | Frost et al. |
| 4,530,356 A | 7/1985 | Helfgott et al. |
| 4,533,818 A | 8/1985 | Green |
| 4,549,554 A | 10/1985 | Markham |
| 4,562,838 A | 1/1986 | Walker |
| 4,644,951 A | 2/1987 | Bays |
| 4,651,753 A | 3/1987 | Lifton |
| 4,669,465 A | 6/1987 | Moore et al. |
| 4,696,298 A | 9/1987 | Higgins et al. |
| 4,708,147 A | 11/1987 | Haaga |
| 4,776,848 A | 10/1988 | Solazzo |
| 4,781,198 A | 11/1988 | Kanabrocki |
| 4,803,341 A | 2/1989 | Barowski et al. |
| 4,817,631 A | 4/1989 | Schnepp-Pesch et al. |
| 4,850,373 A | 7/1989 | Zatloukal et al. |
| 4,871,074 A | 10/1989 | Bryson et al. |
| 4,875,478 A | 10/1989 | Chen |
| 4,886,492 A | 12/1989 | Brooke et al. |
| 4,893,635 A | 1/1990 | De Groot et al. |
| 4,919,146 A | 4/1990 | Rhinehart et al. |
| 4,926,877 A | 5/1990 | Bookwalter |
| RE33,528 E | 7/1990 | Onik et al. |
| 4,973,019 A | 11/1990 | Baird et al. |
| 4,982,739 A | 1/1991 | Hemstreet et al. |
| 4,985,027 A | 1/1991 | Dressel |
| 4,989,614 A | 2/1991 | Dejter, Jr. et al. |
| 4,995,877 A | 2/1991 | Ams et al. |
| 5,027,827 A | 7/1991 | Cody et al. |
| 5,031,778 A | 7/1991 | Edgecombe |
| 5,054,615 A | 10/1991 | Stillwagon et al. |
| 5,057,085 A | 10/1991 | Kopans |
| 5,074,311 A | 12/1991 | Hasson |
| 5,090,649 A | 2/1992 | Tipp |
| 5,108,381 A | 4/1992 | Kolozsi |
| 5,112,299 A | 5/1992 | Pascaloff |
| 5,124,532 A | 6/1992 | Hafey et al. |
| 5,133,359 A | 7/1992 | Kedem et al. |
| 5,141,189 A | 8/1992 | Andrew |
| D329,304 S | 9/1992 | Tipp |
| 5,172,701 A | 12/1992 | Leigh |
| D332,670 S | 1/1993 | McFarland |
| 5,183,052 A | 2/1993 | Terwilliger |
| 5,192,439 A | 3/1993 | Roth et al. |
| 5,195,985 A | 3/1993 | Hall |
| 5,197,484 A | 3/1993 | Kornberg et al. |
| 5,197,968 A | 3/1993 | Clement |
| 5,211,165 A | 5/1993 | Damoulin et al. |
| 5,213,110 A | 5/1993 | Kedem et al. |
| 5,217,478 A | 6/1993 | Rexroth |
| 5,217,479 A | 6/1993 | Shuler |
| 5,226,909 A | 7/1993 | Evans et al. |
| 5,234,000 A | 8/1993 | Hakky et al. |
| 5,243,994 A | 9/1993 | Ranalletta |
| 5,256,160 A | 10/1993 | Clement |
| D342,585 S | 12/1993 | Fischbach et al. |
| 5,275,609 A | 1/1994 | Pingleton et al. |
| 5,281,197 A | 1/1994 | Arias et al. |
| 5,284,156 A | 2/1994 | Schramm et al. |
| 5,285,795 A | 2/1994 | Ryan et al. |
| 5,289,831 A | 3/1994 | Bosley |
| 5,290,303 A | 3/1994 | Pingleton et al. |
| 5,295,980 A | 3/1994 | Ersek |
| 5,307,808 A | 5/1994 | Damoulin et al. |
| 5,312,425 A | 5/1994 | Evans et al. |
| 5,318,025 A | 6/1994 | Damoulin et al. |
| 5,320,110 A | 6/1994 | Wang |
| 5,320,635 A | 6/1994 | Smith |
| 5,353,804 A | 10/1994 | Kornberg et al. |
| 5,358,638 A | 10/1994 | Gershenson |
| 5,399,167 A | 3/1995 | Deniega |
| 5,403,276 A | 4/1995 | Schechter et al. |
| 5,411,513 A | 5/1995 | Ireland et al. |
| 5,415,169 A | 5/1995 | Siczek et al. |
| 5,423,844 A | 6/1995 | Miller |
| 5,429,138 A | 7/1995 | Jamshidi |
| 5,431,645 A | 7/1995 | Smith et al. |
| 5,437,277 A | 8/1995 | Damoulin et al. |
| 5,443,066 A | 8/1995 | Damoulin et al. |
| 5,445,150 A | 8/1995 | Damoulin et al. |

(56) References Cited

U.S. PATENT DOCUMENTS

| | | |
|---|---|---|
| 5,448,022 A | 9/1995 | Rishel |
| 5,455,766 A | 10/1995 | Scheller et al. |
| 5,456,267 A | 10/1995 | Stark |
| 5,458,112 A | 10/1995 | Weaver |
| 5,464,300 A | 11/1995 | Crainich |
| 5,505,210 A | 4/1996 | Clement |
| 5,514,131 A | 5/1996 | Edwards et al. |
| 5,520,635 A | 5/1996 | Gelbfish |
| 5,520,801 A | 5/1996 | Gerber et al. |
| D371,220 S | 6/1996 | Bherens |
| 5,526,822 A | 6/1996 | Burbank et al. |
| 5,531,703 A | 7/1996 | Skwarek et al. |
| 5,541,972 A | 7/1996 | Anthony |
| 5,543,645 A | 8/1996 | Barret et al. |
| 5,543,695 A | 8/1996 | Culp et al. |
| 5,560,373 A | 10/1996 | De Santis |
| 5,575,293 A | 11/1996 | Miller et al. |
| 5,580,347 A | 12/1996 | Reimels |
| D377,996 S | 2/1997 | Gilbert |
| 5,601,585 A | 2/1997 | Banik et al. |
| 5,611,352 A | 3/1997 | Kobren et al. |
| 5,615,782 A | 4/1997 | Choe |
| D379,554 S | 5/1997 | Landers |
| 5,630,939 A | 5/1997 | Bulard et al. |
| 5,643,304 A | 7/1997 | Schechter et al. |
| 5,647,374 A | 7/1997 | Cutrer |
| 5,649,547 A | 7/1997 | Ritchart et al. |
| 5,669,876 A | 9/1997 | Schechter et al. |
| 5,669,923 A | 9/1997 | Gordon |
| 5,678,549 A | 10/1997 | Heywang-Koebrunner et al. |
| D386,818 S | 11/1997 | Boomfield |
| 5,685,840 A | 11/1997 | Schechter et al. |
| 5,689,159 A | 11/1997 | Culp et al. |
| 5,715,822 A | 2/1998 | Watkins et al. |
| 5,730,717 A | 3/1998 | Gelbfish |
| 5,741,272 A | 4/1998 | Kuhne |
| 5,769,086 A | 6/1998 | Ritchart et al. |
| 5,775,333 A | 7/1998 | Burbank et al. |
| 5,779,649 A | 7/1998 | Herbert |
| 5,782,764 A | 7/1998 | Werne |
| 5,782,849 A | 7/1998 | Miller |
| 5,788,651 A | 8/1998 | Weilandt |
| 5,788,673 A | 8/1998 | Young et al. |
| 5,791,908 A | 8/1998 | Gillio |
| 5,794,626 A | 8/1998 | Kieturakis |
| 5,794,799 A | 8/1998 | Collins et al. |
| 5,800,389 A | 9/1998 | Burney et al. |
| 5,804,936 A | 9/1998 | Brodsky et al. |
| 5,810,806 A | 9/1998 | Ritchart et al. |
| 5,817,048 A | 10/1998 | Lawandy |
| 5,827,305 A | 10/1998 | Gordon |
| 5,830,219 A | 11/1998 | Bird et al. |
| 5,843,111 A | 12/1998 | Vijkfinkel |
| 5,848,978 A | 12/1998 | Cecchi |
| 5,853,205 A | 12/1998 | Enomoto et al. |
| D403,810 S | 1/1999 | Owens |
| 5,855,554 A | 1/1999 | Schneider et al. |
| 5,871,454 A | 2/1999 | Majlessi |
| 5,882,305 A | 3/1999 | Dumoulin et al. |
| 5,893,862 A | 4/1999 | Pratt et al. |
| 5,910,139 A | 6/1999 | Cochran et al. |
| 5,911,701 A | 6/1999 | Miller et al. |
| 5,913,857 A | 6/1999 | Ritchart et al. |
| 5,913,863 A | 6/1999 | Fischer et al. |
| 5,916,229 A | 6/1999 | Evans |
| 5,921,943 A | 7/1999 | Kass |
| 5,928,137 A | 7/1999 | Green |
| 5,928,164 A | 7/1999 | Burbank et al. |
| 5,928,218 A | 7/1999 | Gelbfish |
| 5,938,604 A | 8/1999 | Wagner et al. |
| 5,944,673 A | 8/1999 | Gregoire et al. |
| 5,954,670 A | 9/1999 | Baker |
| 5,964,716 A | 10/1999 | Gregoire et al. |
| 5,976,164 A | 11/1999 | Bencini et al. |
| 5,980,469 A | 11/1999 | Burbank et al. |
| 5,980,546 A | 11/1999 | Hood |
| 5,997,560 A | 12/1999 | Miller |
| 6,007,497 A | 12/1999 | Huitema |
| 6,017,316 A | 1/2000 | Ritchart et al. |
| 6,019,733 A | 2/2000 | Farascioni |
| 6,022,324 A | 2/2000 | Skinner |
| 6,022,325 A | 2/2000 | Siczek et al. |
| 6,036,632 A | 3/2000 | Whitmore, III et al. |
| D423,717 S | 4/2000 | Taylor |
| 6,048,321 A | 4/2000 | McPherson et al. |
| 6,050,955 A | 4/2000 | Bryan et al. |
| D426,025 S | 5/2000 | Holmes et al. |
| 6,077,230 A | 6/2000 | Gregoire et al. |
| 6,077,231 A | 6/2000 | Milliman et al. |
| 6,080,113 A | 6/2000 | Heneveld et al. |
| 6,085,749 A | 7/2000 | Wardle et al. |
| 6,086,544 A | 7/2000 | Hibner et al. |
| 6,096,042 A | 8/2000 | Herbert |
| 6,106,512 A | 8/2000 | Cochran et al. |
| 6,109,446 A | 8/2000 | Foote |
| 6,120,462 A | 9/2000 | Hibner et al. |
| 6,120,463 A | 9/2000 | Bauer |
| 6,123,299 A | 9/2000 | Zach, Sr. |
| 6,142,955 A | 11/2000 | Farascioni et al. |
| 6,161,034 A | 12/2000 | Burbank et al. |
| 6,162,187 A | 12/2000 | Buzzard et al. |
| 6,165,137 A | 12/2000 | Milliman et al. |
| 6,174,291 B1 | 1/2001 | McMahon et al. |
| 6,192,583 B1 | 2/2001 | Roffelsen |
| 6,193,414 B1 | 2/2001 | Balzano |
| 6,193,673 B1 | 2/2001 | Voila et al. |
| 6,203,524 B1 | 3/2001 | Burney et al. |
| 6,213,988 B1 | 4/2001 | McIvor et al. |
| 6,245,084 B1 | 6/2001 | Mark et al. |
| 6,251,418 B1 | 6/2001 | Ahern et al. |
| 6,261,241 B1 | 7/2001 | Burbank et al. |
| 6,261,243 B1 | 7/2001 | Burney et al. |
| 6,264,670 B1 | 7/2001 | Chin |
| 6,270,506 B1 | 8/2001 | Sittek et al. |
| 6,272,372 B1 | 8/2001 | Fisher |
| 6,273,862 B1 | 8/2001 | Privitera et al. |
| 6,276,661 B1 | 8/2001 | Laird |
| 6,280,399 B1 | 8/2001 | Rossin et al. |
| 6,289,233 B1 | 9/2001 | Dumoulin et al. |
| 6,293,957 B1 | 9/2001 | Peters et al. |
| 6,321,613 B1 | 11/2001 | Avidor |
| 6,331,165 B1 | 12/2001 | Turturro et al. |
| 6,346,107 B1 | 2/2002 | Cucin |
| 6,347,241 B2 | 2/2002 | Burbank et al. |
| 6,402,701 B1 | 6/2002 | Kaplan et al. |
| 6,416,510 B1 | 7/2002 | Altman et al. |
| 6,428,487 B1 | 8/2002 | Burdorff et al. |
| 6,428,498 B2 | 8/2002 | Uflacker |
| 6,432,045 B2 | 8/2002 | Lemperle et al. |
| 6,432,064 B1 | 8/2002 | Hibner et al. |
| 6,447,477 B2 | 9/2002 | Burney et al. |
| 6,461,350 B1 | 10/2002 | Underwood et al. |
| 6,468,225 B1 | 10/2002 | Lundgren |
| 6,468,227 B2 | 10/2002 | Zimmon |
| 6,471,700 B1 | 10/2002 | Burbank et al. |
| 6,485,436 B1 | 11/2002 | Truckai et al. |
| 6,494,844 B1 | 12/2002 | Van Bladel et al. |
| 6,527,731 B2 | 3/2003 | Weiss et al. |
| 6,558,337 B2 | 5/2003 | Dvorak et al. |
| 6,589,254 B2 | 7/2003 | Fontenot |
| 6,592,508 B1 | 7/2003 | Ravins et al. |
| 6,602,227 B1 | 8/2003 | Cimino et al. |
| 6,626,849 B2 | 9/2003 | Huitema et al. |
| 6,632,182 B1 | 10/2003 | Treat |
| 6,638,235 B2 | 10/2003 | Miller et al. |
| 6,659,338 B1 | 12/2003 | Dittmann et al. |
| 6,675,037 B1 | 1/2004 | Tsekos |
| 6,676,628 B2 | 1/2004 | Sussman et al. |
| 6,676,658 B2 | 1/2004 | Burbank et al. |
| 6,693,552 B1 | 2/2004 | Herzig et al. |
| 6,712,773 B1 | 3/2004 | Viola |
| 6,725,083 B1 | 4/2004 | Burbank et al. |
| 6,730,044 B2 | 5/2004 | Stephens et al. |
| 6,744,824 B1 | 6/2004 | Duvaut et al. |

(56) References Cited

U.S. PATENT DOCUMENTS

| | | |
|---|---|---|
| 6,752,768 B2 | 6/2004 | Burdorff et al. |
| 6,758,824 B1 | 7/2004 | Miller et al. |
| 6,758,848 B2 | 7/2004 | Burbank et al. |
| 6,770,063 B2 | 8/2004 | Goldberg et al. |
| 6,832,988 B2 | 12/2004 | Sproul |
| 6,846,320 B2 | 1/2005 | Ashby et al. |
| 6,863,676 B2 | 3/2005 | Lee et al. |
| 6,889,073 B2 | 5/2005 | Lampman et al. |
| 6,921,943 B2 | 7/2005 | Kenney et al. |
| 6,923,754 B2 | 8/2005 | Lubock |
| 6,942,627 B2 | 9/2005 | Huitema |
| 6,945,942 B2 | 9/2005 | Van Bladel et al. |
| 6,951,611 B2 | 10/2005 | Dannenmaier et al. |
| 6,955,641 B2 | 10/2005 | Lubock |
| 6,969,358 B2 | 11/2005 | Baltschun et al. |
| 6,975,701 B2 | 12/2005 | Galkin |
| 6,999,553 B2 | 2/2006 | Livingston |
| 7,041,217 B1 | 5/2006 | Close et al. |
| 7,044,957 B2 | 5/2006 | Foerster et al. |
| 7,066,893 B2 | 6/2006 | Hibner et al. |
| 7,112,275 B2 | 9/2006 | Hashimoto |
| 7,149,566 B2 | 12/2006 | Lee |
| 7,160,292 B2 | 1/2007 | Moorman et al. |
| 7,171,256 B1 | 1/2007 | Graessle et al. |
| 7,189,207 B2 | 3/2007 | Viola |
| 7,192,404 B2 | 3/2007 | Rhad et al. |
| 7,226,424 B2 | 6/2007 | Ritchart et al. |
| 7,276,032 B2 | 10/2007 | Hibner |
| 7,311,672 B2 | 12/2007 | Van Bladel et al. |
| 7,316,726 B2 | 1/2008 | Schwindt |
| 7,347,829 B2 | 3/2008 | Mark et al. |
| 7,351,210 B2 | 4/2008 | Cicenas et al. |
| 7,351,228 B2 | 4/2008 | Keane et al. |
| 7,402,140 B2 | 7/2008 | Spero et al. |
| 7,415,301 B2 | 8/2008 | Hareyama et al. |
| 7,438,692 B2 | 10/2008 | Tsonton et al. |
| 7,442,171 B2 | 10/2008 | Stephens et al. |
| 7,445,739 B2 | 11/2008 | Tsonton et al. |
| 7,458,940 B2 | 12/2008 | Miller |
| 7,470,237 B2 | 12/2008 | Beckman et al. |
| 7,611,474 B2 | 11/2009 | Hibner et al. |
| 7,641,668 B2 | 1/2010 | Perry et al. |
| 7,645,240 B2 | 1/2010 | Thompson et al. |
| 7,693,567 B2 | 4/2010 | Tsonton et al. |
| 7,699,855 B2 | 4/2010 | Anderson et al. |
| 7,708,751 B2 | 5/2010 | Hughes et al. |
| 7,711,407 B2 | 5/2010 | Hughes et al. |
| 7,727,164 B2 | 6/2010 | Cicenas et al. |
| 7,769,426 B2 | 8/2010 | Hibner et al. |
| 7,787,936 B2 | 8/2010 | Kressy et al. |
| 7,826,883 B2 | 11/2010 | Hibner et al. |
| 7,831,290 B2 | 11/2010 | Hughes et al. |
| 7,914,464 B2 | 3/2011 | Burdorff et al. |
| 7,935,044 B2 | 5/2011 | Lubock |
| 8,016,844 B2 | 9/2011 | Privitera et al. |
| 8,109,885 B2 | 2/2012 | Heske et al. |
| 8,109,886 B2 | 2/2012 | Miller et al. |
| 8,277,474 B2 | 10/2012 | Norman et al. |
| 8,280,490 B2 | 10/2012 | Pfeiler |
| 8,282,573 B2 | 10/2012 | Shabaz et al. |
| 8,932,233 B2 | 1/2015 | Haberstich et al. |
| 9,392,999 B2 | 7/2016 | Haberstich et al. |
| 2001/0032649 A1 | 10/2001 | Nagano |
| 2001/0049502 A1 | 12/2001 | Chen |
| 2002/0120212 A1 | 8/2002 | Ritchart et al. |
| 2003/0004529 A1 | 1/2003 | Tsonton et al. |
| 2003/0097079 A1 | 5/2003 | Garcia |
| 2003/0099307 A1 | 5/2003 | Wu |
| 2003/0109802 A1 | 6/2003 | Laeseke et al. |
| 2003/0199753 A1 | 10/2003 | Hibner et al. |
| 2004/0162505 A1 | 8/2004 | Kaplan et al. |
| 2004/0222145 A1 | 11/2004 | Onoue et al. |
| 2005/0049521 A1 | 3/2005 | Miller et al. |
| 2005/0113715 A1 | 5/2005 | Schwindt et al. |
| 2005/0215922 A1 | 9/2005 | Tsonton et al. |
| 2006/0004258 A1 | 1/2006 | Sun et al. |
| 2006/0009712 A1 | 1/2006 | Van Bladel et al. |
| 2008/0033454 A1 | 2/2008 | Lukoschek et al. |
| 2008/0161720 A1 | 7/2008 | Nicoson et al. |
| 2008/0200834 A1 | 8/2008 | Mark et al. |
| 2008/0200835 A1 | 8/2008 | Mnoson et al. |
| 2008/0300506 A1 | 12/2008 | McIntyre |

FOREIGN PATENT DOCUMENTS

| | | |
|---|---|---|
| CN | 101099684 A | 1/2008 |
| DE | 92 06 853.7 | 10/1992 |
| DE | 42 16 694 | 12/1992 |
| EP | 0 161 606 | 11/1985 |
| EP | 0 378 692 | 7/1990 |
| EP | 0 541 970 | 5/1993 |
| EP | 0 995 400 | 4/2000 |
| EP | 1 356 772 | 10/2003 |
| EP | 1 410 764 | 4/2004 |
| EP | 1 598 006 | 11/2005 |
| EP | 1 598 015 | 11/2005 |
| EP | 2 283 772 | 2/2011 |
| FR | 2 332 743 | 6/1977 |
| GB | 1 252 170 | 11/1971 |
| GB | 2 018 601 | 10/1979 |
| JP | 5101165 B2 | 12/2012 |
| JP | 5456865 B2 | 4/2014 |
| WO | WO 90/08508 | 8/1990 |
| WO | WO 93/14707 | 8/1993 |
| WO | WO 93/17620 | 9/1993 |
| WO | WO 95/25465 | 9/1995 |
| WO | WO 96/14023 | 5/1996 |
| WO | WO 96/32067 | 10/1996 |
| WO | WO 97/24991 | 7/1997 |
| WO | WO 98/06338 | 2/1998 |
| WO | WO 98/22022 | 5/1998 |
| WO | WO 98/25556 | 6/1998 |
| WO | WO 98/55016 | 12/1998 |
| WO | WO 01/54763 | 8/2001 |
| WO | WO 01/82810 | 11/2001 |
| WO | WO 01/97702 | 12/2001 |
| WO | WO 02/13709 | 2/2002 |
| WO | WO 03/026509 | 4/2003 |
| WO | WO 2004/043531 | 5/2004 |
| WO | WO 2005/017775 | 2/2005 |
| WO | WO 2005/112778 | 12/2005 |

OTHER PUBLICATIONS

Encor TM MRI Specifications and Breast Biopsy System, SenoRx, 2005, pp. 1-2.

Heywant-Köbrunner et al. "MR-guided percutaneous excisional and incisional biopsy of breast lesions," Eur. Radiol., vol. 9 (1999) pp. 1656-1665.

Kuhl, C.K. et al., "Interventional Breast MR Imaging: Clinical Use of a Stereotactic Localization and Biopsy Device," Radiology, vol. 204 (1997) pp. 667-675.

Noras Medizimechnik, Operator Manual, Model MR-BI 160, Revision 3, 2000, 11pgs.

Perlot, C. et al., "Multicenter study for the evaluation of a dedicated biopsy device for MR-guided vacuum biopsy of the breast," Eur Radiol., vol. 12 (2002) pp. 1463-1470.

Savitz, M.H., "CT-Guided Needle Procedures for Brain Lesions: 20 Years' Experience," The Mount Sinai Journal of Medicine, vol. 67(4) (Sep. 2000) pp. 318-321.

Savitz, M.H. "Free-hand CT-guided Needle for Biopsy and Drainage of Intracerebral Lesions. Ten Years Experience," Int. Surg., vol. 77 (1992) pp. 211-215.

Viehweg, P. et al., "MR-guided interventional breast procedures considering vacuum biopsy in particular," Eur. J. of Radiol., vol. 42 (2002) pp. 32-39.

Australian Patent Examination Report dated Feb. 21, 2012 for App No. 2007202271.

Australian Patent Examination Report No. 1, dated Jun. 2, 2014, for Application No. AU 2012233005.

(56) References Cited

OTHER PUBLICATIONS

Australian Patent Examination Report No. 2, dated Jun. 3, 2014, for Application No. AU 2012233005.
Canadian Office Action dated Jan. 24, 2014 for Application No. CA 2,589,569.
Canadian Office Action dated Mar. 19, 2015 for Application No. CA 2,589,569.
Canadian Office Action dated May 22, 2012 for Application No. CA 2,508,099.
Canadian Office Action dated Jul. 12, 2013 for Application No. CA 2,508,099.
Canadian Office Action dated Oct. 16, 2014 for Application No. CA 2,508,099.
Office Action dated May 23, 2008 for Chinese Application No. 200510074636.1.
European Search Report dated Jan. 5, 2004 for EPO Application 03252518.0.
European Search Report dated Sep. 20, 2005 for Application No. PCT/US2005/017775.
European Search Report dated Sep. 23, 2005 for Application EP 052543171.
European Search Report dated May 21, 2007 for Application No. 07250438.4, pp. 1-5.
European Search Report dated Sep. 25, 2007 for Application No. 07252089.3.
Indian Office Action dated Apr. 29, 2015 for Application No. 788/KOL/2007, 2 pgs.
International Search Report and Written Opinion dated Oct. 4, 2005 for Application No. PCT/US2005/017775.
Preliminary Patentability Report dated Nov. 21, 2006 for PCT/US2005/017775.
Translation of Japanese Office Action dated Jan. 11, 2012 for App No. 2007134436.
US Office Action dated Jul. 1, 2008 for U.S. Appl. No. 11/463,346.
US Office Action dated Jul. 3, 2008 for U.S. Appl. No. 11/076,612.
US Office Action dated Mar. 21, 2008 for U.S. Appl. No. 11/103,718.
US Office Action dated Apr. 4, 2008 for U.S. Appl. No. 11/103,959.
US Office Action dated Sep. 23, 2008 for U.S. Appl. No. 11/323,535.
Provisional Patent U.S. Appl. No. US 60/573,510, filed May 21, 2004.

MRI BIOPSY DEVICE

CROSS REFERENCE TO RELATED APPLICATIONS

The present application is a continuation of U.S. patent application Ser. No. 14/568,478, titled "MRI BIOPSY DEVICE," filed on Dec. 12, 2014, which is a continuation of U.S. patent application Ser. No. 11/419,567, titled "MRI BIOPSY DEVICE," filed on May 22, 2006, which is a continuation in part of U.S. patent application Ser. No. 11/103,959, "MRI BIOPSY DEVICE LOCALIZATION FIXTURE" to Hughes et al., filed on 12 Apr. 2005, which claims priority to U.S. Provisional Pat. Appln. No. 60/573,510, "MRI BIOPSY DEVICE," filed on May 21, 2004, the disclosure of which is hereby incorporated by reference in its entirety.

FIELD OF THE INVENTION

The present invention relates, in general, to a method of imaging assisted tissue sampling and, more particularly, to an improved method for positioning a biopsy probe with respect to a magnetic resonance imaging (MRI) breast coil for acquiring subcutaneous biopsies and for removing lesions.

BACKGROUND OF THE INVENTION

Core biopsy devices have been combined with imaging technology to better target a lesion in breast tissue. One such commercially available product is marketed under the trademark name MAMMOTOME™, by Ethicon Endo-Surgery, Inc. An embodiment of such a device is described in U.S. Pat. No. 5,526,822 issued to Burbank, et al., on Jun. 18, 1996, and is hereby incorporated herein by reference. Its handle receives mechanical and electrical power as well as vacuum assist from a remotely positioned control module that is spaced away from the high magnetic field of a Magnetic Resonance Imaging (MRI) machine.

As seen from that reference, the instrument is a type of image-guided, percutaneous coring, breast biopsy instrument. It is vacuum-assisted, and some of the steps for retrieving the tissue samples have been automated. The physician uses this device to capture "actively" (using the vacuum) the tissue prior to severing it from the body. This allows the sampling of tissues of varying hardness. In addition, a side opening aperture is used, avoiding having to thrust into a lesion, which may tend to push the mass away, cause a track metastasis, or cause a hematoma that, with residual contrast agent circulating therein, may mimic enhancement in a suspicious lesion. The side aperture may be rotated about a longitudinal axis of the probe, thereby allowing multiple tissue samples without having to otherwise reposition the probe. These features allow for substantial sampling of large lesions and complete removal of small ones.

Vacuum assisted core biopsy devices have been adapted to be safe and compatible with various imaging modalities, including Magnetic Resonance Imaging (MRI). In particular, portions of a biopsy system placed near the magnet core of an MRI machine need to be nonresponsive to the strong magnetic field to prevent becoming drawn toward the magnet core or to malfunction. Further, the MRI machine depends upon sensing extremely weak radio frequency (RF) signals emanated by tissue after being excited by a strong change in the magnetic field. Components placed in the RF shielded MRI suite need to avoid producing electromagnetic interference (EMI) and need to avoid having materials that would distort RF signals sufficient to create artifacts in the MRI scan data.

A successful approach has been to segregate motive power generation, graphical user interface, vacuum assist, and closed loop control in a control module that has typically been placed about 6 feet away from the magnet core to mitigate detrimental interaction with its strong magnetic field and/or sensitive radio frequency (RF) signal detection antennas. An intuitive graphical user interface (GUI) provides a range of preprogrammed functionality incorporated into a control module to efficiently use time in an MRI suite to take tissue samples.

As an example, in U.S. Pat. No. 6,752,768, the disclosure of which is hereby incorporated by reference in its entirety, a control button may be depressed to change a mode of operation of a core biopsy device with this mode displayed remotely on a display.

While a full function GUI has numerous clinical benefits, the clinician may find the control module inconveniently remote during hands-on portions of the procedure. In addition, some MRI machines have such increased sensitivity and/or increased magnet field strength that it is desirable to increase the distance of the control monitor (e.g., 30 feet) from the MRI machine. Further, even if the control monitor is sufficiently close, some clinicians prefer a simplified user interface to simplify training familiarity.

Consequently, a significant need exists for a biopsy system compatible for use in an MRI suite with biopsy controls with enhanced convenience and intuitiveness.

BRIEF SUMMARY OF THE INVENTION

The invention overcomes the above-noted and other deficiencies of the prior art by providing a handpiece of a magnetic resonance imaging (MRI) compatible core biopsy system that includes a graphical user interface that facilitates user control even with vacuum, power generation, and control processing components remotely positioned away from the MRI magnet and sensitive radio frequency (RF) receiving components. Thereby, a clinician may have the full functionality of vacuum assisted core biopsy systems yet not be inconvenienced by the distance from a remotely positioned control module.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

An MRI biopsy device advantageously includes is partially disposable for sterility purposes with a reusable portion for economy. Inconvenience of mechanical, electrical, and pneumatical coupling to a remotely placed control portion, necessitated by a strong magnetic field and sensitive RF receiving components of an MRI machine, is mitigated. First, proximal detachable intuitive controls and displays on the MRI biopsy device give interactive control even after insertion into localizing and guiding structures. Second, binding of mechanical coupling to the MRI biopsy device is sensed prior to equipment damage or malfunction. Third, mechanical coupling is moved closer to engagement points between the MRI biopsy device and guiding structures to reduce torque loads, especially those transferred through its distal probe. Fourth, a single mechanical drive cable drives a fixed ratio transmission that translates and rotates a cutter of the distal probe to realize an effective fixed ratio translation/rotation sampling cut without the encumbrance of two mechanical drive cables.

Figure 1:
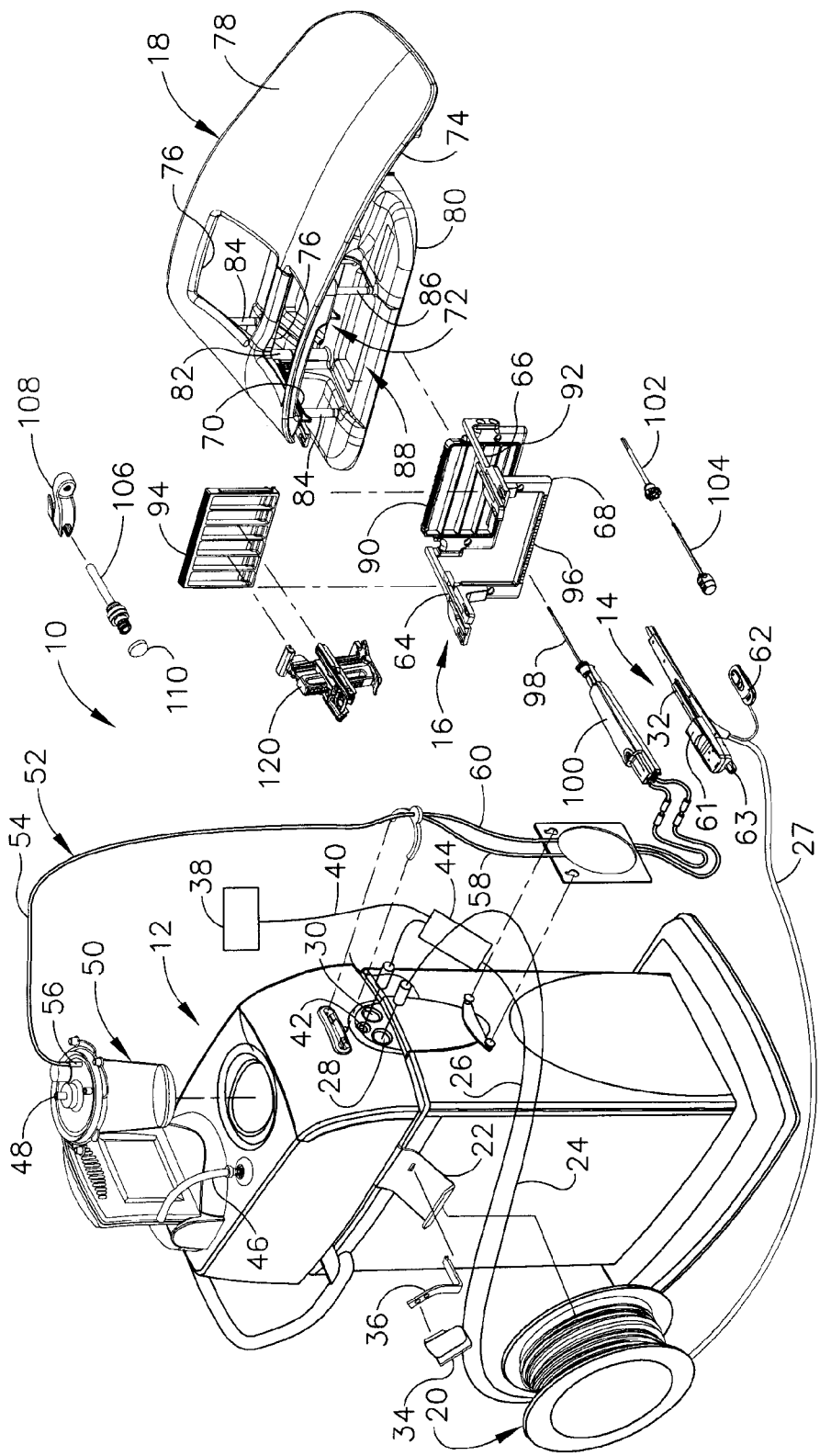
FIG. 1 is a perspective disassembled view of a Magnetic Resonance Imaging (MRI) biopsy system including a handpiece ("biopsy device") having intuitive graphical controls consistent with aspects of the invention.
Figure 2:
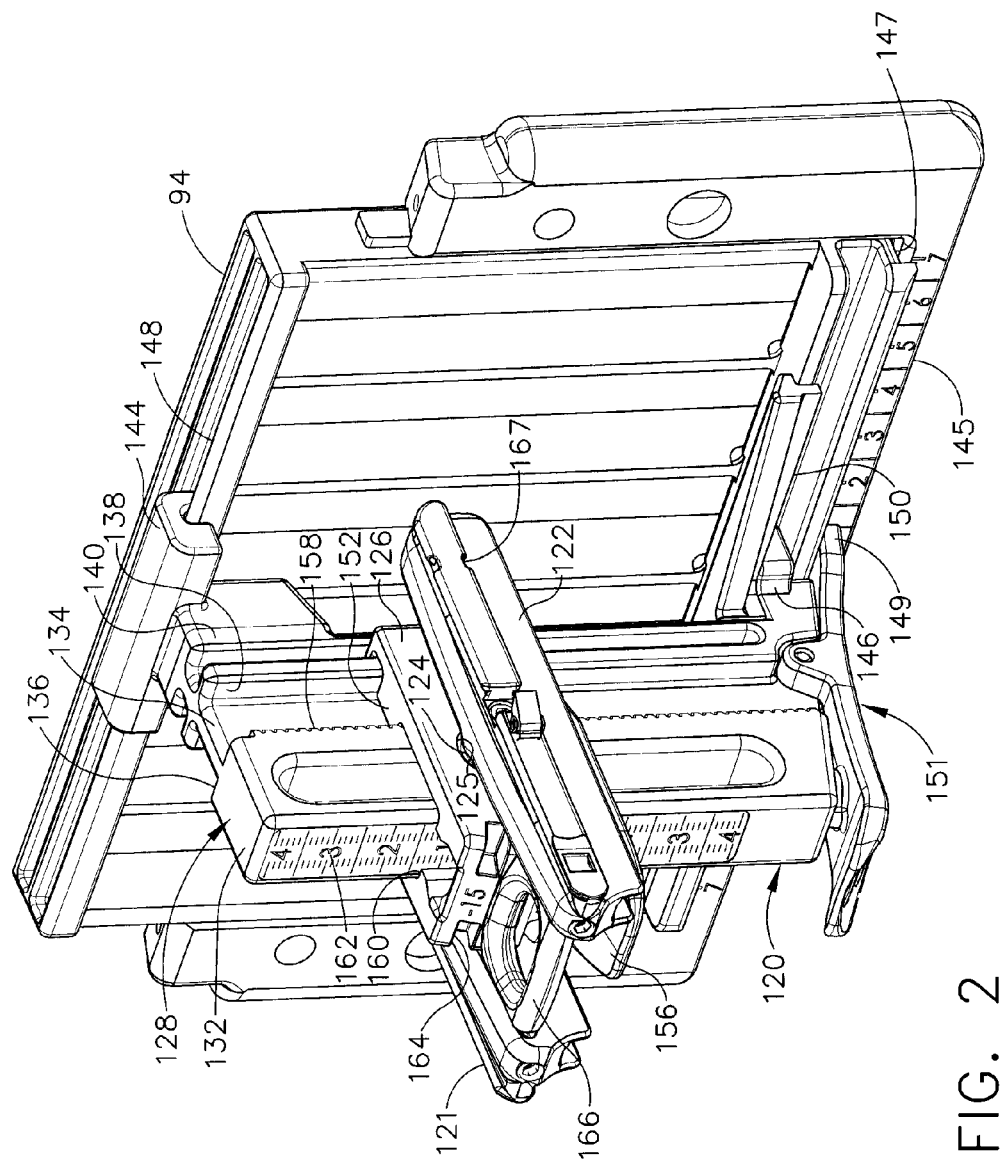
FIG. 2 is an isometric view of a lateral fence and pedestal of a localization fixture of the MRI biopsy system of FIG. 1.
Figure 3:
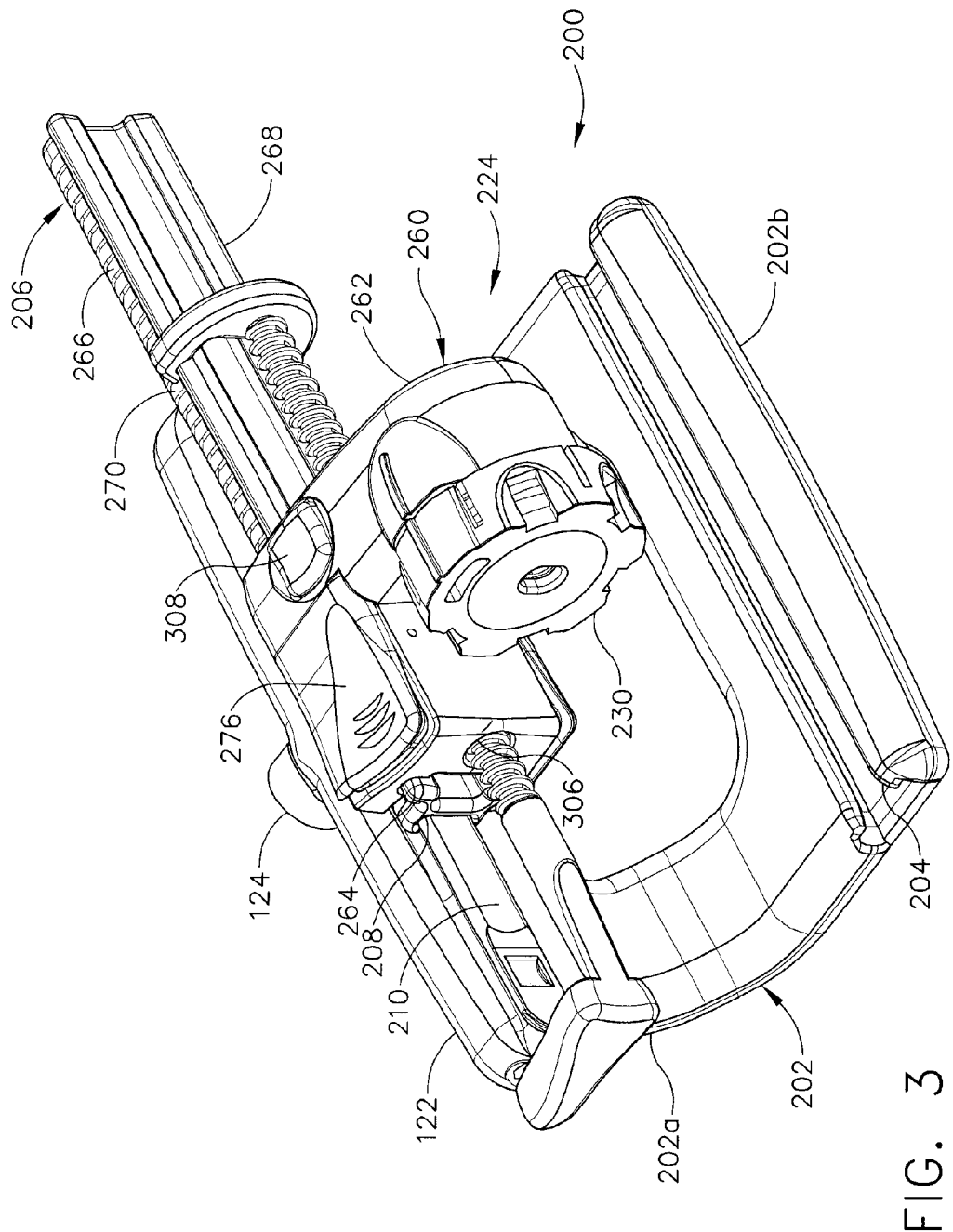
FIG. 3 is an isometric view of a guidance assembly mounted on a right primary targeting rail of FIG. 2.

Turning to the Drawings, wherein like numerals denote like components throughout the several views, in FIGS. 1-3, a Magnetic Resonance Imaging (MRI) compatible biopsy system 10 has a control module 12 that typically is placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality is incorporated into the control module 12 to assist in taking these tissue samples. The control module 12 controls and powers an MRI biopsy device ("handpiece") 14 that is positioned and guided by a localization fixture 16 attached to a breast coil 18 that is placed upon a gantry (not shown) of the MRI machine.

A cable management spool 20 is placed upon a cable management attachment saddle 22 that projects from a side of the control module 12. Wound upon the cable management spool 20 is a paired electrical cable 24 and mechanical cable 26 which are bundled into sheathed cable 27 for communicating control signals and cutter rotation/advancement motions respectively. In particular, electrical and mechanical cables 24, 26 each have one end connected to respective electrical and mechanical ports 28, 30 in the control module 12 and another end connected to a reusable holster portion 32 of the MRI biopsy device 14. An MRI docking cup 34, which may hold the holster portion 32 when not in use, is hooked to the control module 12 by a docking station mounting bracket 36.

An interface lock box 38 mounted to a wall provides a tether 40 to a lockout port 42 on the control module 12. The tether 40 is advantageously uniquely terminated and of short length to preclude inadvertent positioning of the control module 12 too close to the MRI machine. An in-line enclosure 44 may advantageously register the tether 40, electrical cable 24 and mechanical cable 26 to their respective ports 42, 28, 30 on the control module 12.

Vacuum assist is provided by a first vacuum line 46 that connects between the control module 12 and an outlet port 48 of a vacuum canister 50 that catches liquid and solid debris. A tubing kit 52 completes the pneumatic communication between the control module 12 and the MRI biopsy device 14. In particular, a second vacuum line 54 is connected to an inlet port 56 of the vacuum canister 50. The second vacuum line 54 divides into two vacuum lines 58, 60 that are attached to the MRI biopsy device 14. With the MRI biopsy device 14 installed in the holster portion 32, the control module 12 performs a functional check. Saline is manually injected into biopsy device 14 to serve as a lubricant and to assist in achieving a vacuum seal. The control module 12 actuates a cutter mechanism (not shown) in the MRI biopsy device 14, monitoring full travel. Binding in the mechanical cable 26 or within the biopsy device 14 is monitored with reference to motor force exerted to turn the mechanical cable 26 and/or an amount of twist in the mechanical cable 26 sensed in comparing rotary speed or position at each end of the mechanical cable 26.

Just proximal to a display area 61 on the reusable holster portion 32, a remote keypad 62, which is detachable from the reusable holster portion 32, communicates via the electrical cable 24 to the control module 12 to enhance clinician control of the MRI biopsy device 14, especially when controls that would otherwise be on the MRI biopsy device 14 itself are not readily accessible after insertion into the localization fixture 16 and/or placement of the control module 12 is inconveniently remote (e.g., 30 feet away). An aft end thumbwheel 63 on the reusable holster portion 32 is also readily accessible after insertion to rotate the side from which a tissue sample is to be taken.

Left and right parallel upper guides 64, 66 of a localization framework 68 are laterally adjustably received respectively within left and right parallel upper tracks 70, 72 attached to an under side 74 and to each side of a selected breast aperture 76 formed in a patient support platform 78 of the breast coil 18. A base 80 of the breast coil 18 is connected by centerline pillars 82 that are attached to the patient support platform 78 between the breast apertures 76. Also, a pair of outer vertical support pillars 84, 86 on each side spaced about a respective breast aperture 76 respectively define a lateral recess 88 within which the localization fixture 16 resides.

In FIGS. 1-2, a selected breast is compressed along an inner (medial) side by a medial plate 90 downwardly received into a medial three-sided frame 92 of the localization framework 68. The breast is compressed from an outside (lateral) side of the breast by a lateral fence 94 downwardly received into a lateral three-sided frame 96 of the localization framework 68, defining an X-Y plane. The X-axis is vertical (sagittal) with respect to a standing patient and corresponds to a left to right axis as viewed by a clinician facing the externally exposed portion of the localization fixture 16.

Perpendicular to this X-Y plane extending toward the medial side of the breast is the Z-axis, which typically corresponds to the orientation and depth of insertion of a probe 98 of a disposable probe assembly 100 of the MRI biopsy device 14 or of a sleeve trocar 102 with inserted introducer obturator 104. For clarity, the term Z-axis may be used interchangeably with "axis of penetration", although the latter may or may not be orthogonal to the spatial coordinates used to locate an insertion point on the patient. Versions of the localization fixture 16 described herein allow a nonorthogonal axis of penetration to the X-Y axis to a lesion at a convenient or clinically beneficial angle. An origin of the spatial coordinates may be imaging the dents imparted to the tissue by the lateral fence 94. Alternatively, a disposable fiducial pointer 106 held by a fiducial holder 108 is filled with an MRI imagable material (e.g., KY jelly, saline, gadolinium) and sealed with a cap 110.

The probe 98, sleeve trocar 102 and fiducial pointer 106 are guided by the localization fixture 16. With particular reference to FIG. 2, a lateral fence supported pedestal 120 spatially positions left and right primary targeting rails 121, 122 that in turn guide the fiducial pointer 106, the sleeve/trocar 102, or the probe 98 of the biopsy device 14 (FIG. 1). The primary targeting rails 121, 122 each include an attachment axle 124 that receives in either a left or right side axle hub 125 of a (Y-axis) height yoke 126 that is vertically adjustable upon a pedestal main body 128, that in turn is laterally adjustable upon the lateral fence 94. Alternatively, a breast coil may enable mounting the pedestal main body on the medial plate 90 for accessing medially. The pedestal main body 128 includes a proximal upright rectangular column 132 with a thinner wall 134 projecting from its distal side that flares laterally outward (defining left and right vertical rectangular slots 136, 138) as part of a bracket 140 with top and bottom hanger arms 144, 146 that slide laterally respectively on a top track 148 and a proximally open lower track 150 formed in the lateral fence 94. A lateral (X-axis) adjustment lever 151 may be raised to lift its distal end 149 out of engagement with a bottom track 147 formed in the lateral fence 94 as the lateral adjustment lever 151 is repositioned to the left or right to a desired location with reference to a lateral measurement guide 145.

The height yoke 126 is a rectangular cuff interrupted in a mid-portion of a distal side to form locking left and right hands 152 respectively which ride vertically in the left and right vertical rectangular slots 136, 138. The locking left and right hands 152 have respective ridged proximal surfaces (not shown) that are selectively drawn proximally into locking engagement by a height locking lever 156 with a ridged surface 158 on a proximal side of each vertical rectangular slot 136, 138. Lifting the height locking lever 156 takes the height yoke 126 out of locking engagement to the pedestal main body 128 as the height yoke 126 is vertically repositioned. For height adjustment, the proximal top surface of the height yoke 126 serves as a sight 160 to read a height measurement scale 162 presented on a proximal surface of the height locking lever 156.

The attachment axle 124 allows rotation so that an axis of penetration may include an upward or downward trajectory. In the illustrative version, proximal corners of the height yoke 126 include angle detents 164 (e.g., −15°, 0°, +15°) that are selectable by an angle lock lever 166. The primary targeting rail 122 includes a distal detent 167 that serves as a home reference for the fiducial holder 108 (FIG. 1).

Figure 4:
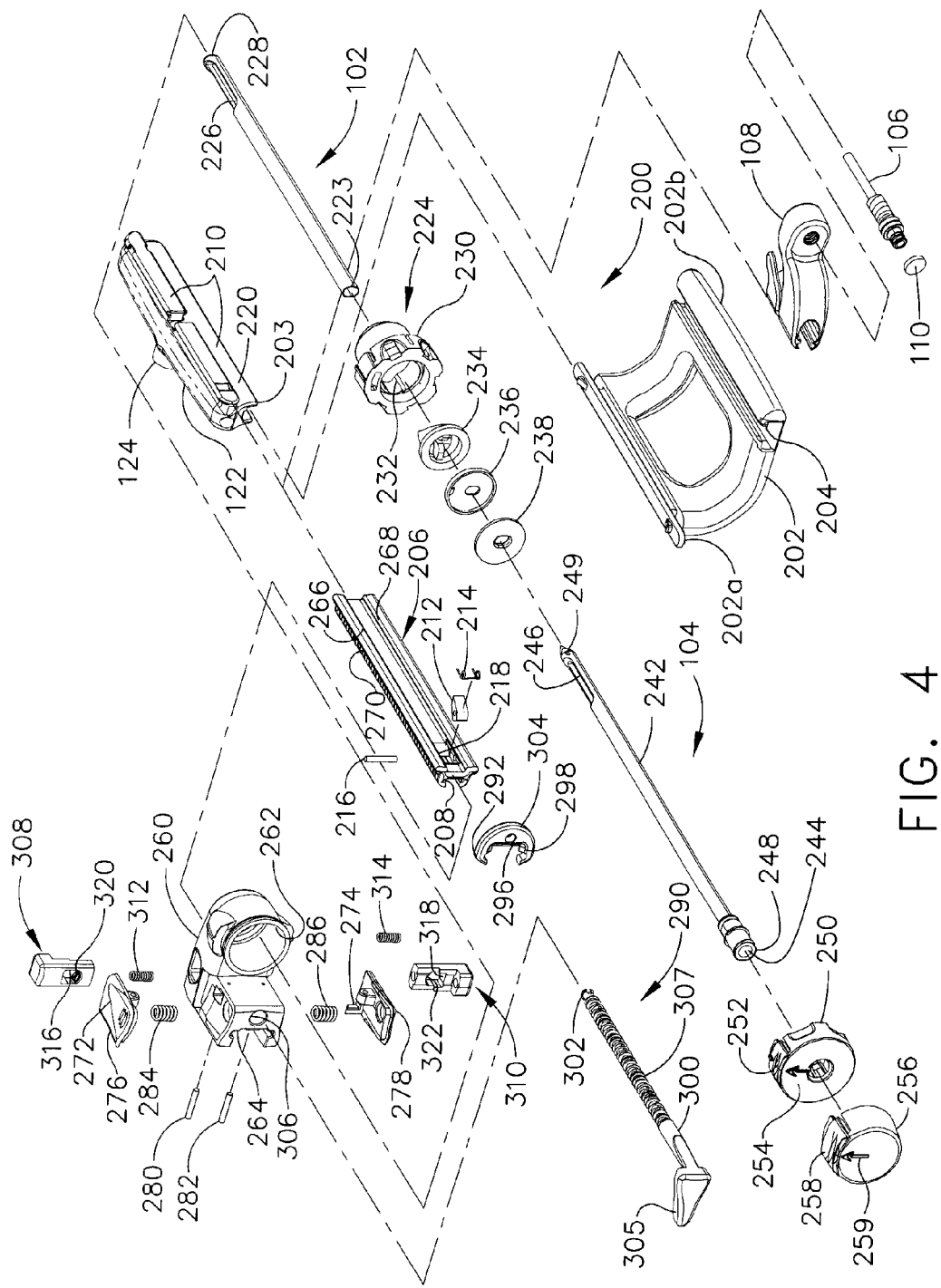
FIG. 4 is an exploded isometric view of the guidance assembly of FIG. 3 and the sleeve trocar and introducer obturator of FIG. 1.

In FIGS. 3-4, a guidance assembly 200, that may be attached to the lateral fence supported pedestal 120 of FIG. 2, includes a cradle 202 whose upper lateral side 202a flares upwardly to engage a bottom channel 203 of the primary targeting rail 122. A lower lateral side 202b flares horizontally to provide a holster guide track 204 that underlies the axis of penetration. To provide additional guidance to the MRI biopsy device 14 (FIG. 1), a secondary targeting rail 206 includes a lateral channel 208 that is guided along a longitudinal guide tab 210 of the primary targeting rail 122. When fully engaged thereon, a pawl 212 pivoting under urging of a pawl spring 214 about a vertical pawl pin 216 in a lateral window 218 proximally positioned in the secondary targeting rail 206 drops into a proximal detent 220 proximally positioned on the primary targeting rail 122. The pawl spring 214 may maintain the pawl 212 in a neutral position that serves in both assembly and later removal of the secondary targeting rail 206 or comprises a pair of opposing pawl springs (not shown) for that purpose.

Figure 5:
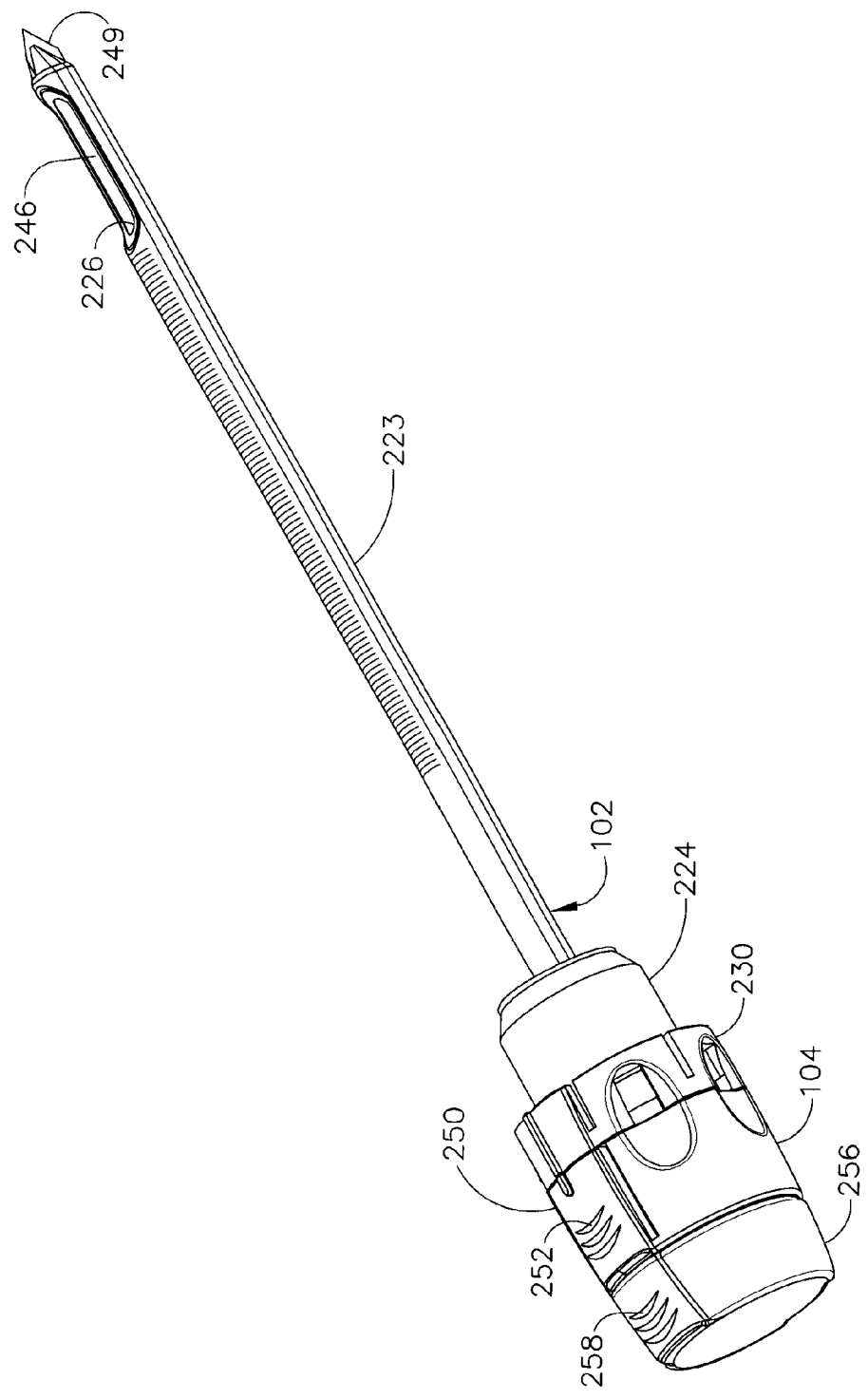
FIG. 5 is an isometric view of the introducer obturator inserted into the sleeve trocar of FIGS. 1 and 4.

In FIGS. 4-5, the sleeve trocar 102 includes a hollow shaft (or cannula) 223 that is proximally attached to a cylindrical hub 224 and has a lateral aperture 226 proximate to an open distal end 228. The cylindrical hub 224 has an exteriorly presented thumbwheel 230 for rotating the lateral aperture 226. The cylindrical hub 224 has an interior recess 232 that encompasses a duckbill seal 234, wiper seal 236 and a seal retainer 238 to provide a fluid seal when the shaft 223 is empty and for sealing to the inserted introducer obturator 104.

The introducer obturator 104 advantageously incorporates a number of components with corresponding features. A hollow shaft 242 includes a fluid lumen 244 that communicates between an imageable side notch 246 and a proximal port 248. The hollow shaft 242 is longitudinally sized to extend when fully engaging a piercing tip 249 out of the distal end 228 of the sleeve trocar 102. An obturator handle 250 encompasses the proximal port 248 and includes a locking feature 252, which includes a visible angle indicator 254, that engages the sleeve thumbwheel 230 to ensure that the imageable side notch 246 is registered to the lateral aperture 226 in the sleeve trocar 102. An obturator seal cap 256 may be engaged proximally into the obturator handle 250 to close the fluid lumen 244. The obturator seal cap 256 includes a locking or locating feature 258 that includes a visible angle indicator 259 that corresponds with the visible angle indicator 254 on the obturator thumbwheel cap 230. The obturator seal cap 256 may be fashioned from either a rigid, soft, or elastomeric material.

Returning to FIGS. 3, 4, the sleeve trocar 102 is guided, during penetration of tissue, by a sleeve mount 260 having a sleeve hub 262 that receives the cylindrical hub 224 of the sleeve trocar 102. The sleeve mount 260 has a lateral sleeve hub channel 264 that slides along top and bottom guide flanges 266, 268 of the secondary targeting rail 206, each having an aligned and recess ridged, ratcheting surface 270 that interacts with a respective top and bottom ratcheting feature 272, 274 on respective top and bottom rail lock rocker latches 276, 278 that are engaged by respective top and bottom latch pins 280, 282 in respective sides of the sleeve mount 260. The ratcheting features 272, 274 are proximally ramped such as to allow distal movement. Distal portions of each rail lock rocker latches 276, 278 are biased away from the sleeve mount 260 by respective rail lock compression springs 284, 286 to bias the ratcheting features 272, 274 into contact with the ridges surfaces 270 of the guide flanges 266, 268. Simultaneous depression of the rail lock rocker latches 276, 278 allow the sleeve mount 260 to be drawn proximally, withdrawing any sleeve trocar 102 supported therein, until the sleeve mount 260 reaches a proximal end of the secondary targeting rail 206, whereupon the sleeve mount 260 rotates the pawl 212 clockwise (as viewed from the top) and is thus engaged to the secondary targeting rail 206 as the secondary targeting rail 206 is unlocked from the primary targeting rail 122, causing removal therefrom with continued proximal movement.

Before mounting the secondary targeting rail 206 onto the primary targeting rail 122 in the first place, the sleeve mount 260 is advantageously adjustably positioned on the secondary targeting rail 206 to set a desired depth of penetration. In particular, a depth guide 290 is formed by a crescent-shaped depth indicator 292 having a lateral channel 296 shaped to engage the top and bottom guide flanges 266, 268. Forward ramped surfaces 298 on the top and bottom of the lateral channel 296 are positioned to engage the ridged ratcheting surfaces 270 on the secondary targeting rail 206, allowing assembly by inserting the depth indicator 292 from a distal end of the secondary targeting rail 206. Frictional engagement thereafter resists further proximal movement and strongly opposes any distal movement, especially from a depth lead screw 300 of the depth guide 290, whose distal end 302 rotates within an outboard hole 304 in the depth indicator 292 and whose proximal end deflects laterally as a depth actuator lever 305 is used to rotate and longitudinally position the depth lead screw 300 therein. A mid portion of the depth lead screw 300 is received in a longitudinal through hole 306 formed in the sleeve mount 260 outboard of its lateral channel 208. For coarse depth adjustment, outer lead threads 307 on the depth lead screw 300 selectively engage the sleeve mount 260 until top and bottom coarse adjust buttons 308, 310 are inwardly depressed into the sleeve mount 260, compressing respective top and bottom coarse adjust compression springs 312, 314. Each coarse adjust button 308, 310 includes a respective vertically elongate aperture 316, 318 whose inward surface presents a worm gear segment 320, 322 to engage the outer lead threads 307 on the depth lead screw 300 when urged into engagement by relaxed coarse adjust compression screws 312, 314.

Returning to FIG. 3, the thumbwheel 230 is depicted as engaged to the sleeve hug 262 of the sleeve mount 260 with other portions of the sleeve trocar 102 omitted. Applications consistent with the present invention may include a probe of an MRI biopsy device that includes a piercing tip or that otherwise is used without passing through a hollow shaft (cannula) 223. As such, the thumbwheel with similar sealing members may be incorporated into the sleeve mount 260.

Figure 6:
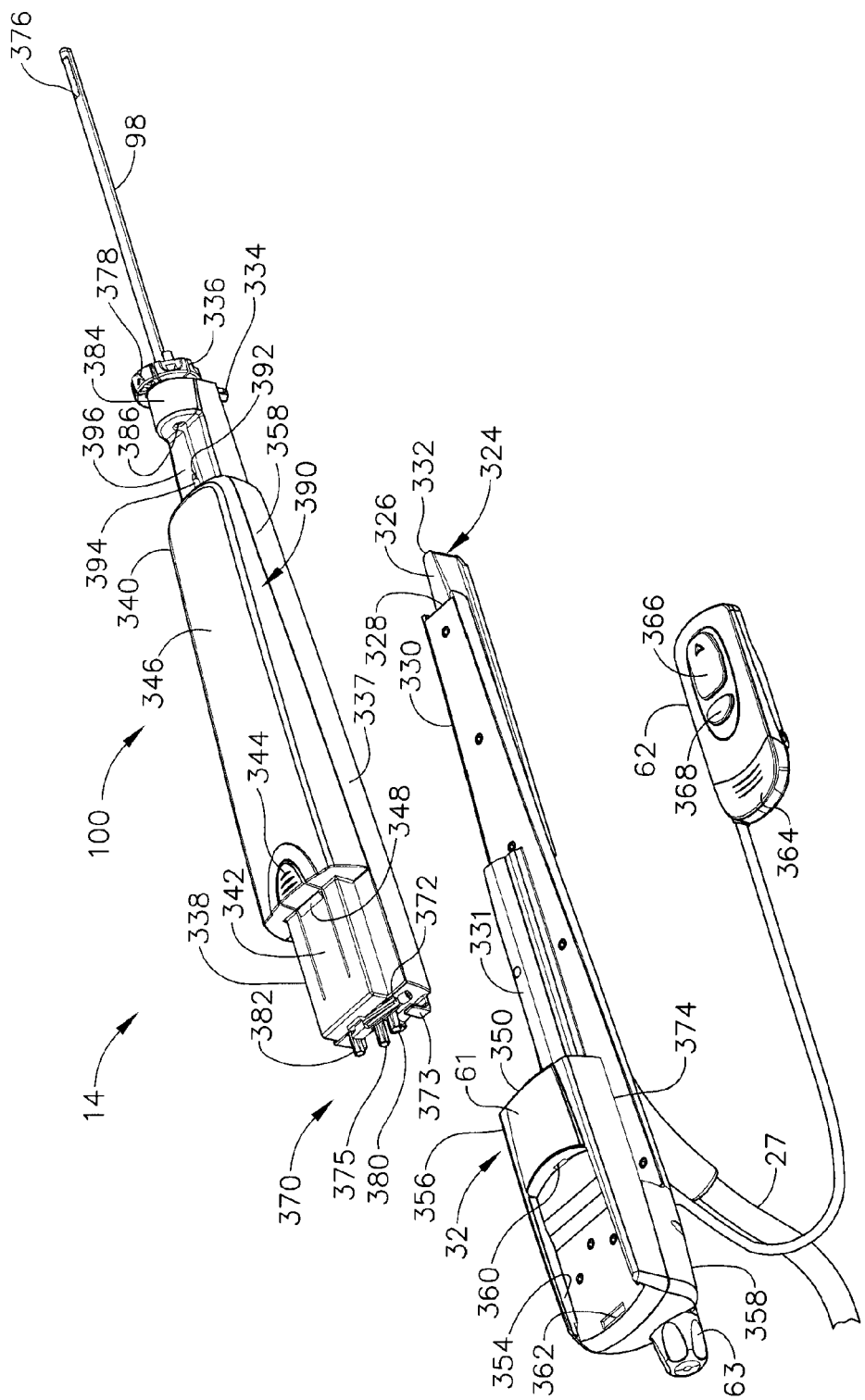
FIG. 6 is an aft right isometric view of the MRI biopsy device of FIG. 1 with a disposable probe assembly and keypad control disengaged from a reusable holster portion.
Figure 7:
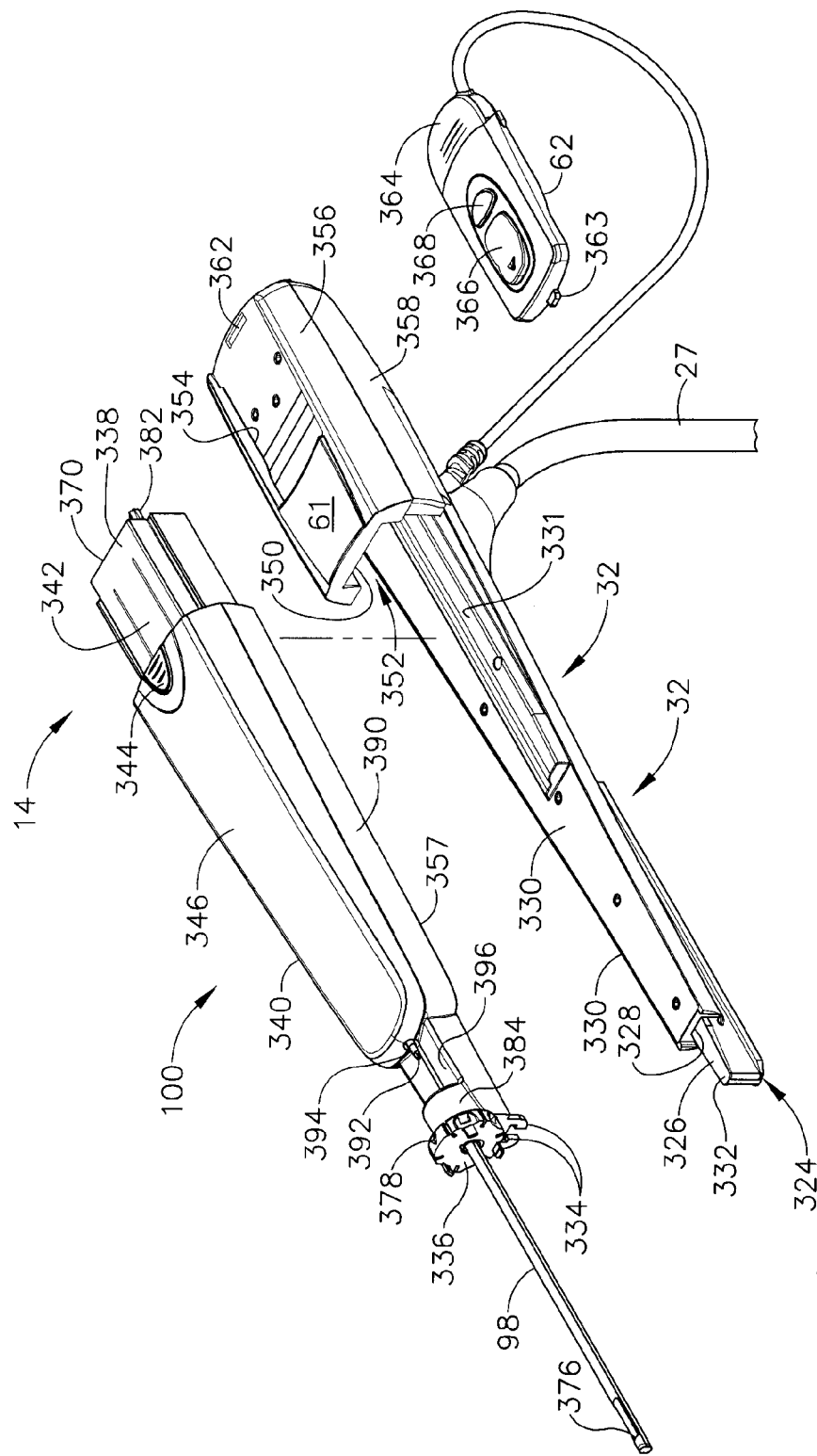
FIG. 7 is a fore left isometric view of the MRI biopsy device of FIG. 1 with the disposable probe assembly and keypad control disengaged from the reusable holster portion.

In FIGS. 6-7, the MRI biopsy device 14 has the disposable probe assembly 100 depicted detached from the reusable holster portion 32 and with the remote keypad 62 released from the reusable holster portion 32. The sheathed cable 27 is joined to an underside of the reusable holster portion 32 distal to the aft end thumbwheel 63 to enhance balance and support of the reusable holster portion, which in turn may be engaged to the holster guide track 204 (FIG. 4) by an I-beam shaped holster rail 324 whose upper surface 326 is engaged within a bottom channel 328 of a holster base plate 330. A ridged member 331 upon the holster base plate 330 guides the disposable probe assembly 100 during engagement. A narrowed upper distal surface 332 of the holster rail 324 also engages downward gripping flanges 334 extending downward just proximal to a distal thumbwheel 336 of the disposable probe assembly 100. An under slung shell 337 is fastened to the proximal undersurface portion of the holster base plate 330.

The disposable probe assembly 100 also has an undersurface that backwardly slides into engagement with the reusable holster portion 32. In particular, a narrowed proximal end 338 is formed into an upper cover 340 with a distal locking arm 342 separated from the upper cover 340 on each side except proximally to present an unlocking button 344 on an exposed surface 346 of the upper cover 340 that is depressed to disengage a locking surface 348 (FIG. 6) from a distal lip 350 of a distally open receiving aperture 352 in the reusable holster portion 32 of the holster plate 330.

A recessed deck 354 in an upper proximal surface of a proximal top cover 356 of the reusable holster portion 32 is shaped to receive the remote keypad 62. A lower shell 358 mates to the proximal top cover 356. The proximal top cover 356 also defines the upper portion of the receiving aperture 352. The recessed deck 354 has a front guide hole 360 and a back locking aperture 362 registered to respectively receive a front tooth 363 and a flexing unlock tab 364 at an aft end of the remote keypad 62 to selectively engage and disengage the keypad 62 from the reusable holster portion 32. The keypad 62 also includes a translation rocker button 366 that has a distal advance, a default neutral, and an aft retract command position. An aft button 368 may be programmed for mode functions such as saline flush.

With particular reference to FIG. 6, the disposable probe assembly 100 has a plurality of interconnections presented on an aft docking end 370. A rightward canted vacuum hose nib 372 is positioned to receive a vacuum conduit (not shown) that would be gripped by a friction clip 373 extending under and aft thereof to prevent inadvertent release. A right side slot 374 is distally open and formed between the holster base plate 330 and proximal top cover 356 to receive such a vacuum conduit as the disposable probe assembly 100 is engaged to the reusable holster portion 32. A center splined driveshaft 375 engages the aft end thumbwheel 63 and communicates with the distal thumbwheel 336 to rotate a side aperture 376 in probe 98 to a desired side, as visually confirmed by an arrow indicator 378 on the distal thumbwheel 336. A right splined driveshaft 380 effects cutter translation and a left splined driveshaft 382 effects cutter rotation.

The distal thumbwheel 336 and probe 98 are mounted to a cylindrical hub 384, which is a distal portion of the lower shell 358 that extends beyond the mating with the upper cover 340. A sample through hole 386 communicates through the cylindrical hub 384 for receiving a rotating and translating cutter tube 388 (FIG. 9) that enters the probe 98 and for receiving tissue samples (not shown) deposited by a retracting cutter tube 388. As the cutter tube 388 fully retracts into a carriage cavity 390 formed between the upper cover 340 and proximal portion of the lower shell 358, a distally extending tip 392 from a vacuum tube 394 encompassed by the cutter tube 388 dislodges the retracted tissue sample onto a sample retrieval platform 396, which is a relieved area between the upper cover 340 and the cylindrical hub 384.

Figure 8:
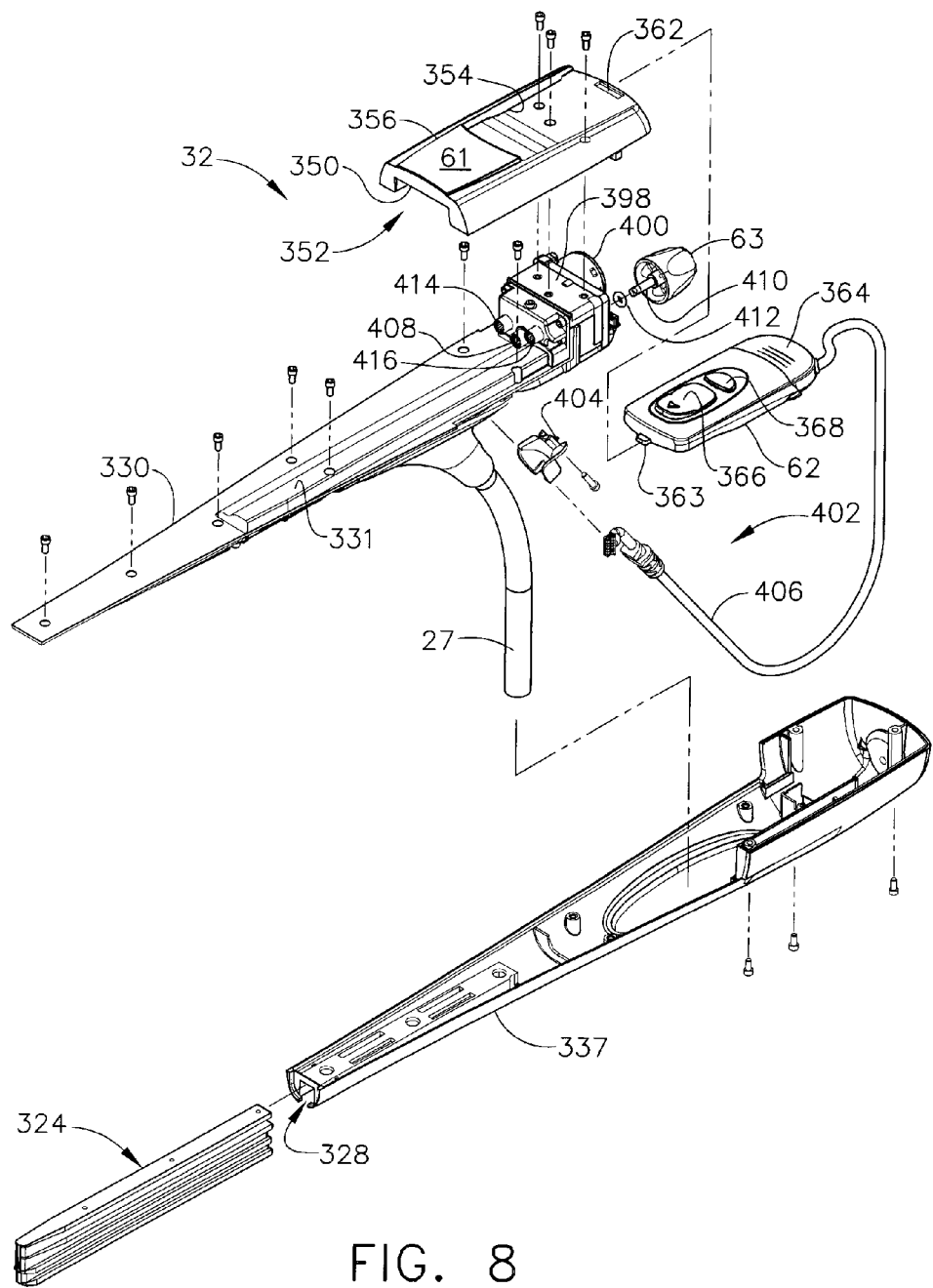
FIG. 8 is a fore left exploded isometric view of the reusable holster portion of FIG. 7.

In FIG. 8, it should be appreciated that the sheathed cable 27 connects to the holster base plate 330 and communicates a single mechanical drive rotation to a fixed ratio transmission 398 mounted to the holster base plate 330 and electrically communicates with an encoder 400 coupled to the fixed ratio transmission 398 aft of the receiving aperture 352. The sheathed cable 27 also communicates electrically with the display area 61 via a wire bundle (not shown) and with the keypad 62 via a cable assembly 402, the latter including a strain relief bracket 404 that grips a keypad cable 406 and is fastened proximate to the sheathed cable 27. The fixed ratio transmission 398 has a pass-through port 408 that receives a distal end the center splined driveshaft 375 (FIG. 6) to rotatingly engage a proximally received beveled shaft 410 distally presented by the aft end thumbwheel 63 and sealed by an O-ring 412. A right port 414 distally presented by the fixed ratio transmission 398 engages for rotation the right splined driveshaft 380 from the disposable probe assembly 100 for advancing and retracting ("translation") the cutter tube 388. A left port 416 distally presented by the fixed ratio transmission 398 engages for rotation the left splined driveshaft 382 from the disposable probe assembly 100 for rotating the cutter tube 388 when a distal cutting edge of the cutter tube 388 slides past the side aperture 376 of the probe 98.

Figure 9:
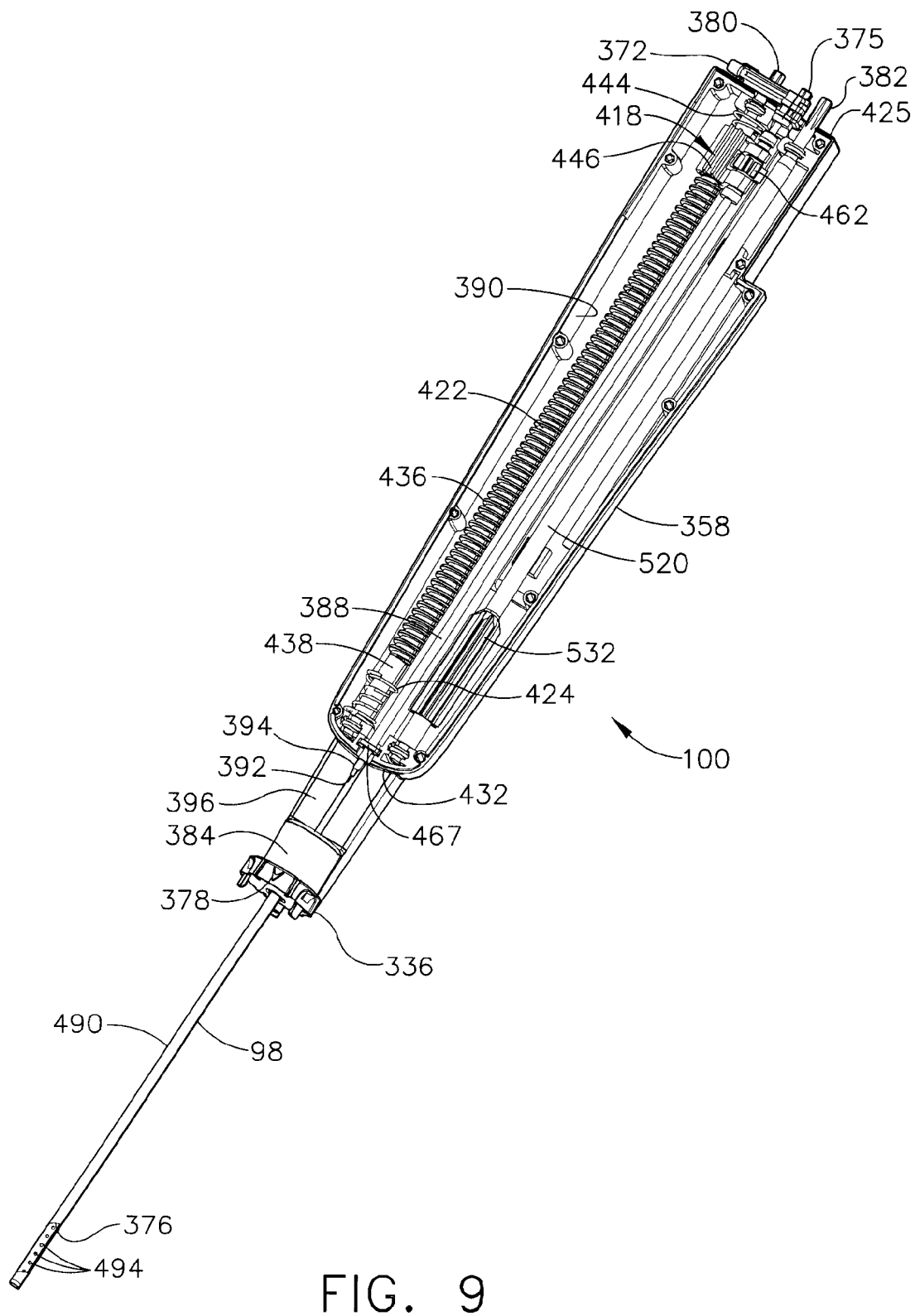
FIG. 9 is a top view of the disposable probe assembly of FIG. 7 with an upper cover removed to expose interior components of a carriage cavity.
Figure 10:
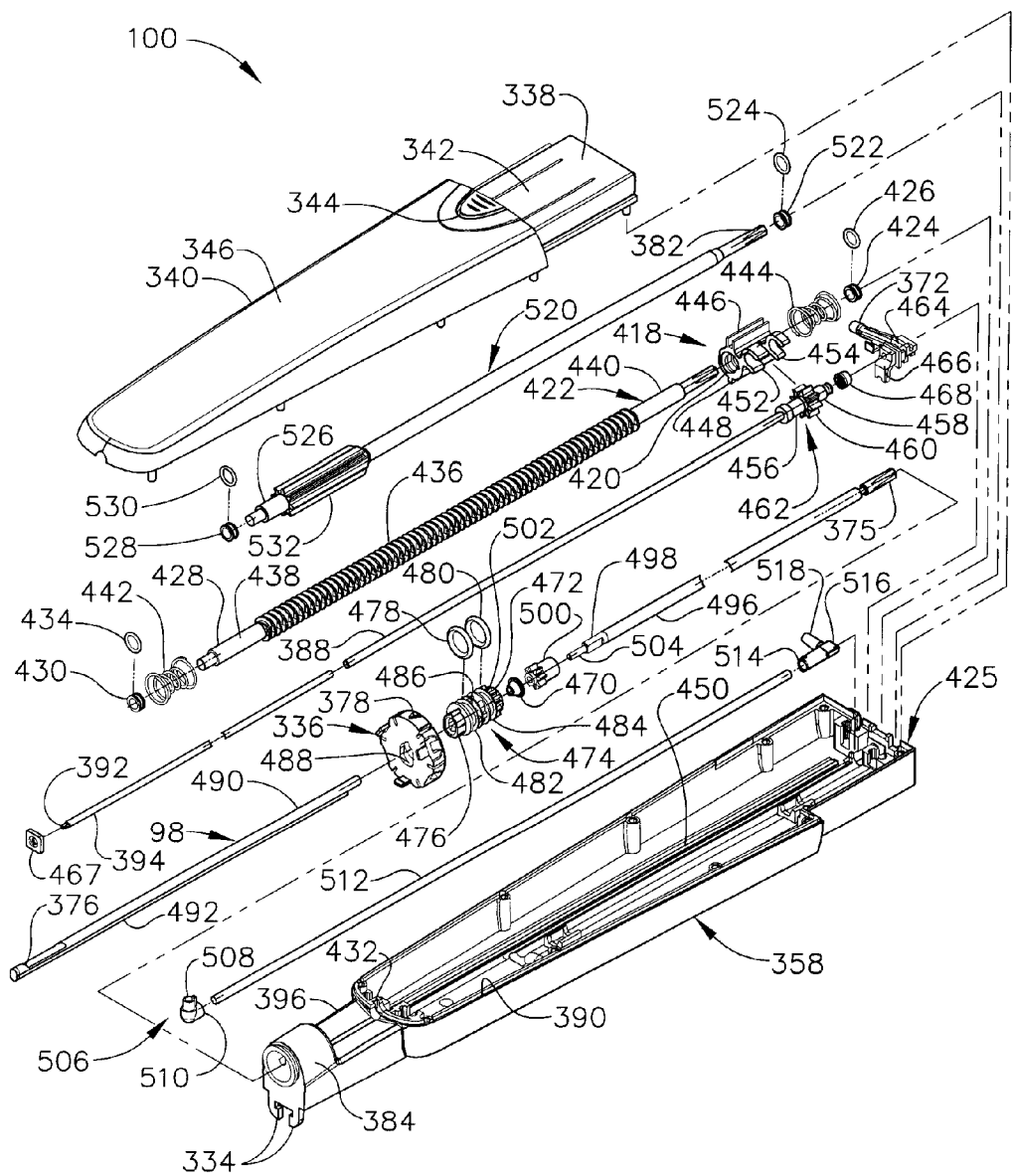
FIG. 10 is a fore left exploded isometric view of the disposable probe assembly of FIG. 7.

In FIGS. 9-10, the carriage cavity 390 of the disposable probe assembly 100 includes a cutter carriage 418 having a threaded longitudinal bore 420 that encompasses an elongate translation shaft 422 whose proximal termination is the right splined driveshaft 380 supported by an aft right cylindrical bearing 424 received in an aft wall 425 of the lower shell 358. A race about the outer circumference of the cylindrical bearing 424 receives an O-ring 426. A distal end 428 of the threaded translation shaft 422 rotates within a distal right cylindrical bearing 430 engaged to a forward wall 432 of the lower shell 358. A race about the outer circumference of the cylindrical bearing 430 receives an O-ring 434. A threaded central portion 436 of the elongate translation shaft 422 resides between an unthreaded distal over-run portion 438 and an unthreaded proximal over-run portion 440, both sized to allow the threaded longitudinal bore 420 of the cutter carriage 418 to disengage from the threaded central portion 436.

A distal compression spring 442 and a proximal compression spring 444 respectively reside on the unthreaded distal and proximal over-run portions 438, 440 to urge the threaded longitudinal bore 420 of the cutter carriage 418 back into engagement with the threaded central portion 436 upon reversal of rotation of the elongate translation shaft 422. In particular, the cutter carriage 418 includes a top longitudinal channel 446 that slidingly engages an undersurface of the upper cover 340 (not shown) and a bottom longitudinal guide 448 that engages a longitudinal track 450 on a top surface of the lower shell 358. Thus rotationally constrained, rotation of the elongate translation shaft 422 causes corresponding longitudinal translation of the cutter carriage 418 with distal and aft pairs of gripping flanges 452, 454 maintained laterally to the left to engage respectively distal and proximal races 456, 458 formed on each side of a toothed portion 460 of a cutter spur gear 462, which has a longitudinal bore for applying vacuum.

To that end, the vacuum hose nib 372 is attached to a mounting structure 464 that is gripped between the upper cover 340 and the lower shell 358 to present an orifice 466 within the carriage cavity 390 that is aligned with the longitudinal bore of the cutter gear 462 and that is in fluid communication with the vacuum hose nib 372.

With particular reference to FIG. 10, the proximal end of the vacuum tube 394 is received in the orifice 466. A rectangular guide 467 supports the distally extending tip 392 of the vacuum tube 394 and is engaged between the upper cover 340 and the lower shell 358. The cutter tube 388 encompasses and translates relative to the vacuum tube 394. A seal cap 468 attached to a proximal end of the cutter gear 462 dynamically seals to the outer circumference of the vacuum tube 394 so that vacuum pressure supplied proximate to the distally extending tip 392 is not released within the carriage cavity 390. The cutter tube 388 is advanced around the open distal end of the vacuum tube 394, across the sample retrieval platform 396 to seal against a back seal 470 that substantially closes a proximal opening 472 into a sleeve union 474 that rotates within the cylindrical hub 384. The sleeve union 474 has a distal end 476 engaged for rotation with the distal thumbwheel 336. Distal and proximal O-rings 478, 480 reside respectively within distal and proximal races 482, 484 that straddle a lateral passage 486 of the sleeve union 474 to provide a degree of frictional resistance against inadvertent rotation and advantageously seal the lateral passage 486 for vacuum assistance to prolapse tissue and to retract samples. A noncircular opening 488 is centered in a distal face of the distal thumbwheel 336. A proximal end of a probe tube 490 of the probe 98 extends through the noncircular opening 488 to receive a distal end of the cutter tube 388. A lateral tube 492 attached along its length to the probe tube 490 communicates with the lateral passage 486 of the union sleeve 474. The lateral tube 492 defines a lateral lumen that communicates with the a cutter lumen defined by the probe tube 490/cutter tube 388 below the side aperture 376 through lumen holes 494 (FIG. 9).

The center splined driveshaft 375 that is turned by the aft end thumbwheel 63 rotates in turn a shaft 496 whose keyed distal end 498 in turn is engaged to and rotates a pinion gear 500 that is in gear engagement to a proximal spur gear 502 that forms an outer proximal circumference of the sleeve union 474. A cylindrical distal tip 504 of the keyed distal end 498 rotates within an axle hole (not shown) in the lower shell 358. Rotation of the aft end thumbwheel 63 thus rotates the probe 98.

A distal elbow pneumatic fitting 506 is supported in the lower shell 358 to have an upper end 508 communicating with the lateral passage 486 of the sleeve union 474 and an aft end 510 attached to a vent pneumatic conduit 512 supported by the lower shell 358. The other end of the vent pneumatic conduit 512 is attached to a distal end 514 of a proximal elbow pneumatic fitting 516 whose lateral end 518 is open to atmosphere. Sizing of various components that vent atmospheric pressure through the lumen holes 494 from the lateral end 518 are such that a tissue sample may be withdrawn through the probe tube 490. Yet a greater pneumatic draw of air through the vacuum hose nib 372 prior to severing a tissue sample results in a sufficient low pressure at the side aperture 376 to prolapse tissue for severing.

An elongate rotation shaft 520 proximally terminates in the left splined driveshaft 382 that is supported for rotation by a left aft cylindrical bearing 522 having a race about an outer circumference that receives an O-ring 524 and is received in the aft wall 425 of the lower shell 358. A distal end 526 of the elongate rotation shaft 520 is received for rotation in a left distal cylindrical bearing 528 having a race about an outer circumference that receives an O-ring 530 and that is received within the front wall 425 of the lower shell 358. As the cutter carriage 418 advances to position the cutter tube 388 to slide past the side aperture 376, the cutter spur gear 460 engages a spur gear portion 532 of the elongate rotation shaft 520. Rotating the cutter tube 388 in proportion to an amount of rotation advantages secures an effective severing of tissue. Eliminating rotation when not severing advantageously enhances retraction of tissue sample retraction.

Figure 11:
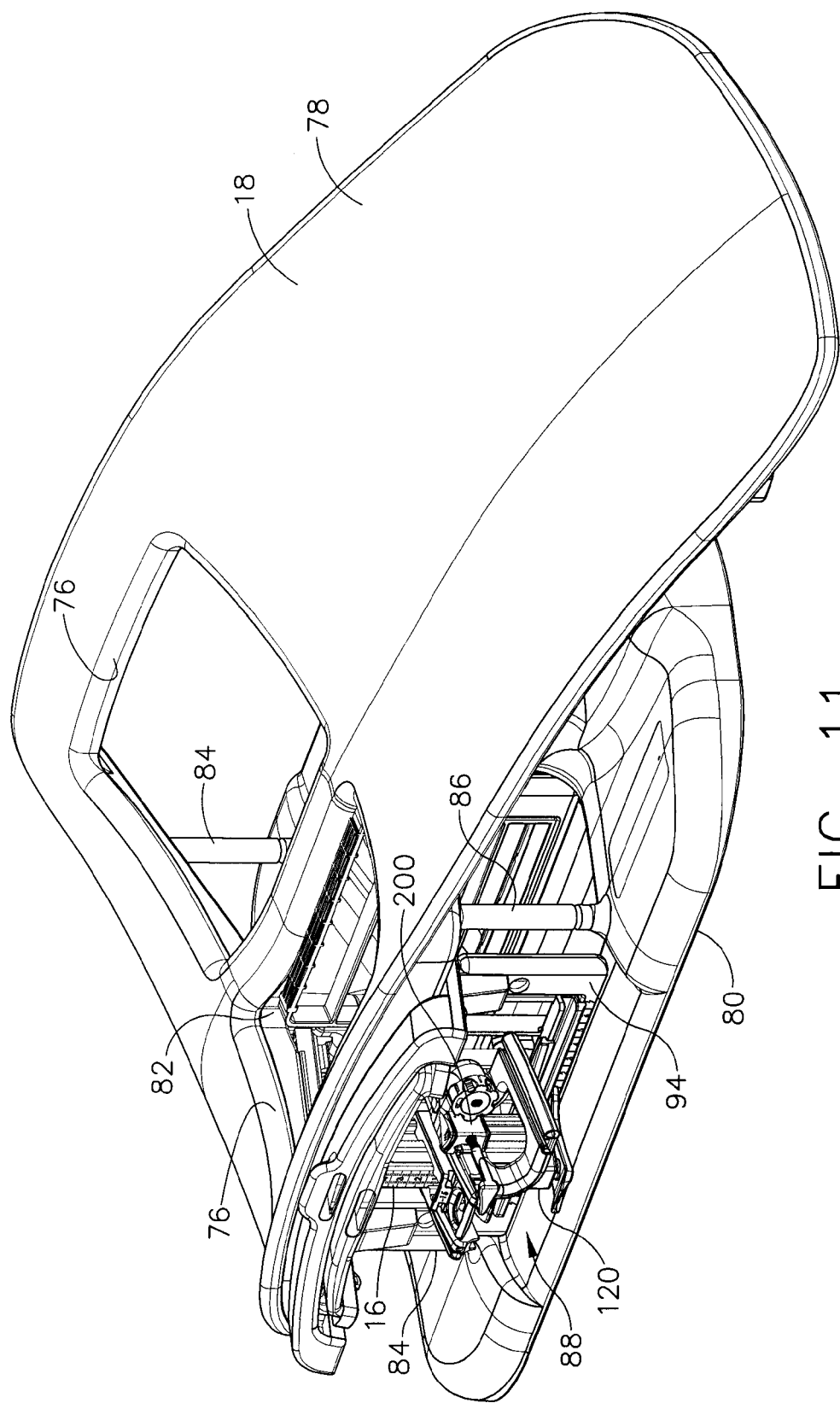
FIG. 11 is an aft left isometric view of the localization fixture and guidance assembly installed into a breast coil of FIG. 1.
Figure 12:
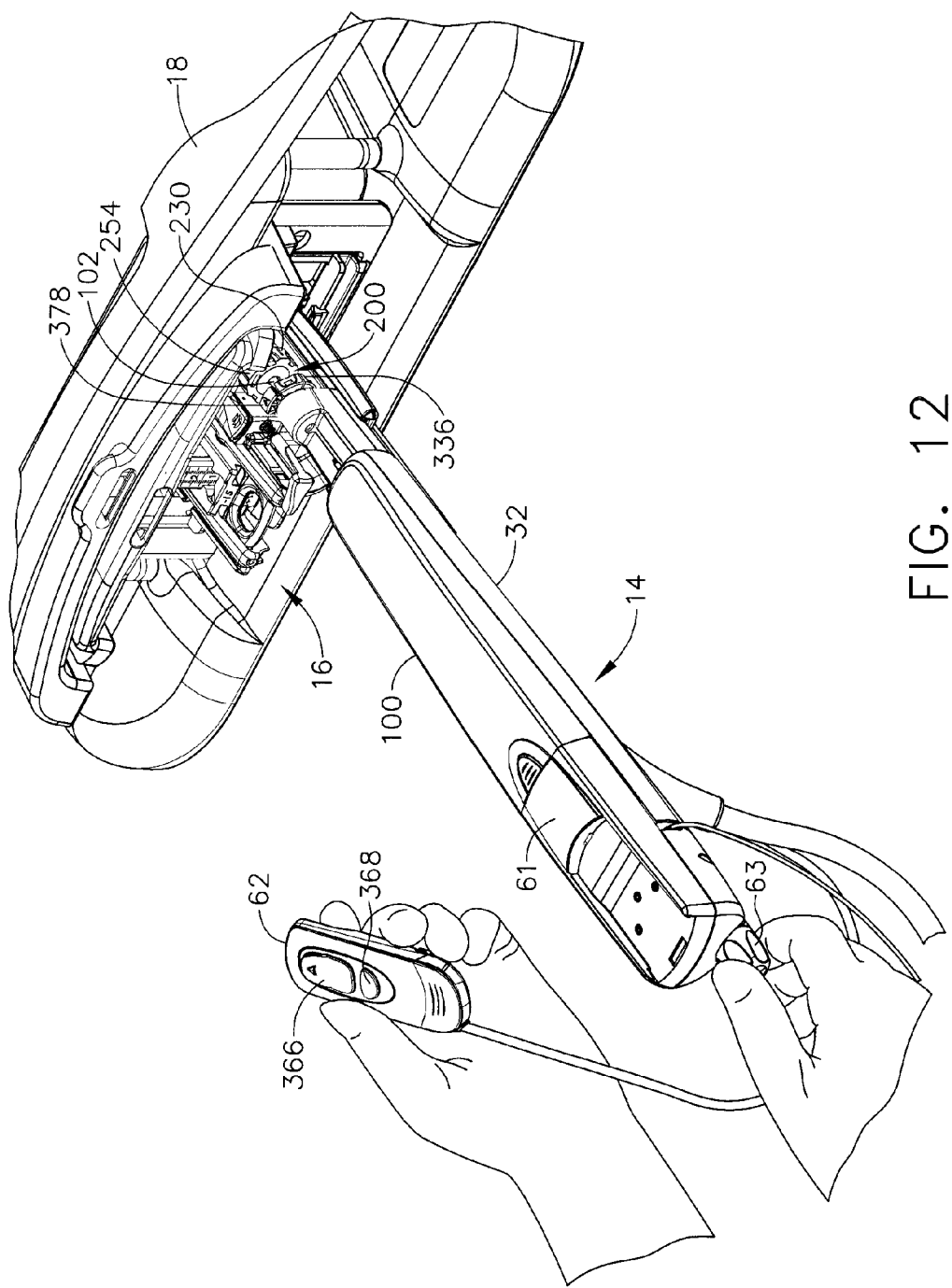
FIG. 12 is an aft isometric view of the MRI biopsy device of FIG. 7 into the guidance assembly of FIG. 11.
Figure 13:
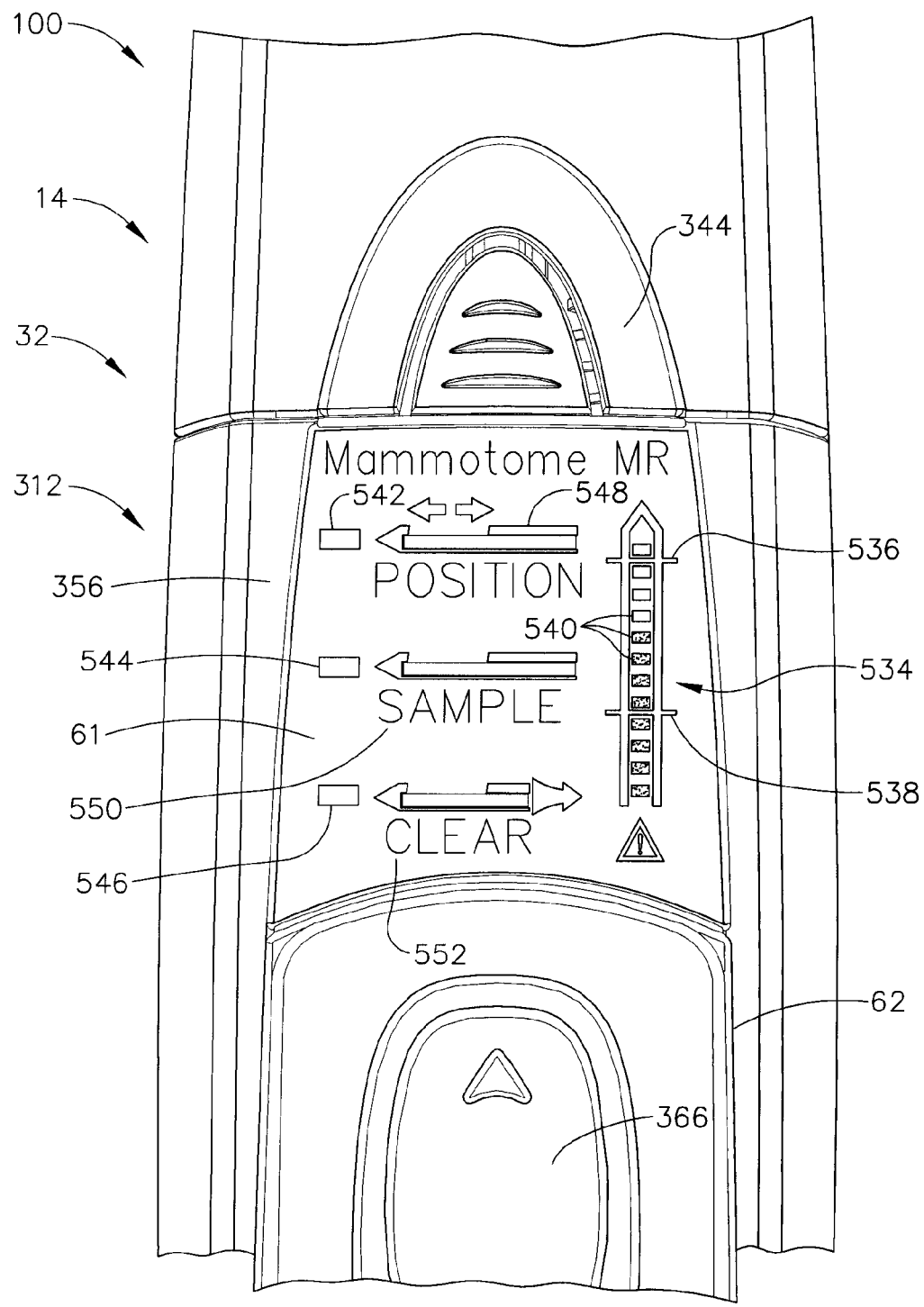
FIG. 13 is a top detail view of a display portion of the MRI biopsy device of FIG. 7.
Figure 14:
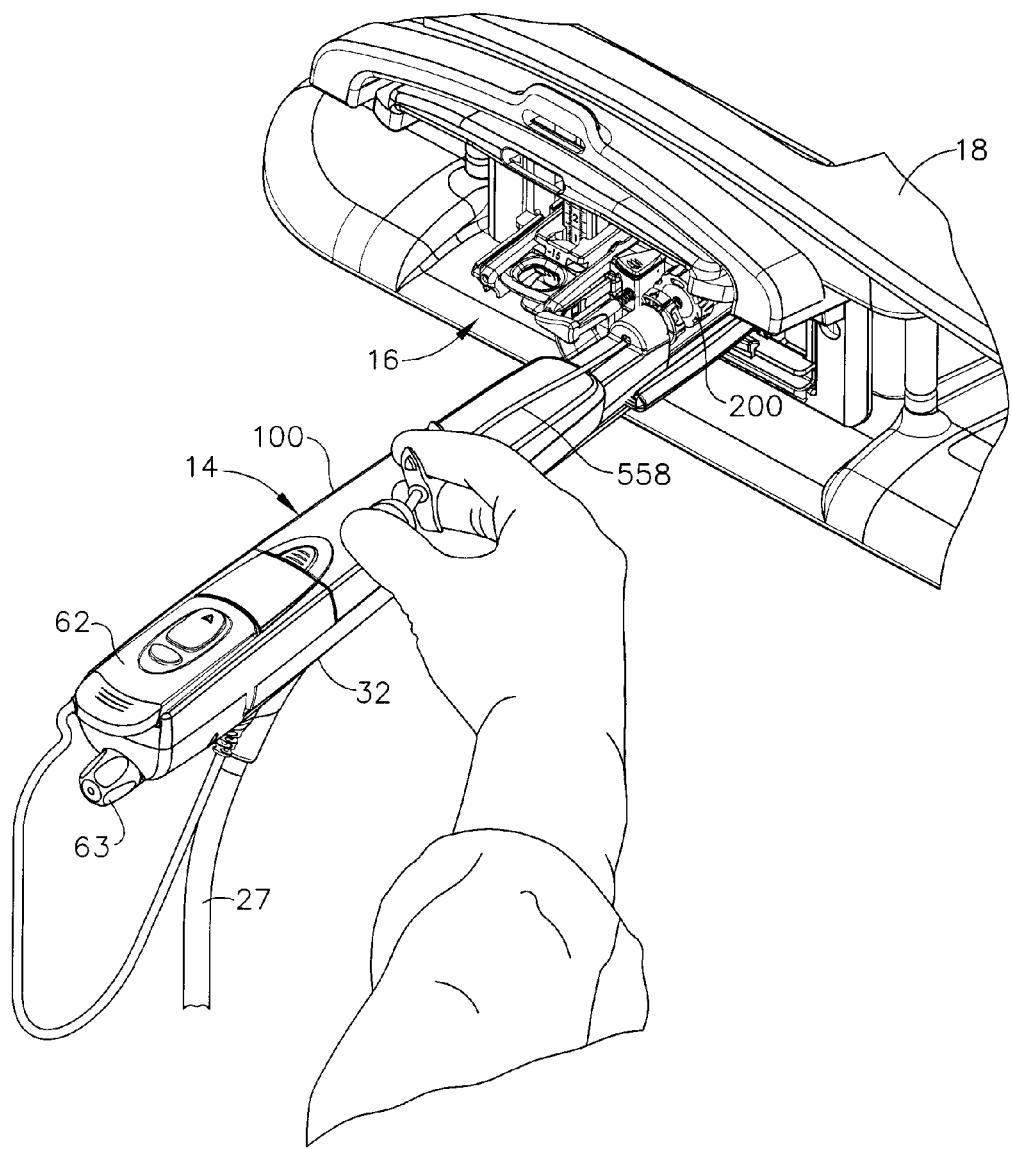
FIG. 14 is an aft right isometric view of the MRI biopsy device, localization fixture and breast coil of FIG. 12 with insertion of a marker deploying instrument through a probe of the disposable probe assembly.

In use, in FIG. 11, the localization fixture 16 has been installed into the breast coil 18. The guidance assembly 200 has been preset for a desired insertion point, a desired axis of penetration, and a depth of penetration. After the sleeve trocar 102/introducer obturator 104 have been inserted and imaged to confirm placement, the introducer obturator 104 is removed and the probe 98 of the biopsy device 14 is inserted, as depicted in FIG. 12. The shape of the sleeve trocar 102 aligns the probe 98, visually assisted by lining up the arrow indicator 378 on the distal thumbwheel 336 with the visible angle indicator on the thumbwheel 230 of the sleeve trocar 102. The surgeon may effect operation of the biopsy device 14 by depressing the translation rocker button 366 and aft button 368 on the keypad 62 while referencing status information about the biopsy device 14 on the display area 61. In FIG. 13, the display area 61 advantageously includes a cutter position bar graph 534 having distal and proximal indications 536, 538 that may be compared with how many light segments 540 have been illuminated to indicate progress of the cutter tube 388 relative to the side aperture 376. The aft button 368 may be toggled to cycle the biopsy device 14 through three modes, indicated by a position LED indicator 542, a sample LED indicator 544, and a clear LED indicator 546 with a corresponding label that graphically depicts operation of the biopsy device in that mode. In particular, a position mode depiction 548 illustrates that the cutter tube 388 may be advanced and retracted, for instance, closing the side aperture 376 prior to insertion of the probe 98 into the sleeve trocar 102. In a sample mode depiction 550, vacuum assistance is implemented, drawing sufficient air through the cutter tube 388 to prolapse tissue into the open side aperture 376 that is maintained while translating the cutter tube 388. In a clear mode depiction 552, vacuum is maintained while fully retracting the cutter tube 388 to retract a tissue sample. In FIG. 14, a marker device 548 is deployed through the sample through hole 386 in the cylindrical hub 388.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while closed loop feedback sensing of a component that is related to cutter tube position has various advantages, determination of cutter position may be achieved in other ways consistent with the present invention. For instance, loading on drive components may be sensed at either full advancement and/or full retraction which are used to calibrate an estimate cutter position based on duration of a translation command.

As another example, rather than discrete LED indicators and labeled depictions, applications consistent with aspects of the invention may include a graphical display (e.g., organic liquid crystal display) that is capable of interactive presentations of intuitive instrument status information. Alternatively or in addition, a touch screen capability may be incorporated to allow instrument control input as well as display.

For another example, applications consistent with aspects of the present invention may be used in conjunction with different diagnostic imaging modalities (e.g., ultrasonic, computed tomography (CT).

What is claimed is:

1. A biopsy device comprising:
    (a) an outer cannula having a lateral tissue receiving aperture;
    (b) an inner tubular cutter disposed for translation within the cannula; and
    (c) a graphical display attached proximally relative to the outer cannula, wherein the graphical display is operable to depict a translation position of the cutter in response to translation of the cutter.

2. The biopsy device of claim 1, wherein the graphical display comprises a bar graph annotated with longitudinal extents of the lateral tissue receiving aperture relative to indicated translation position of the inner tubular cutter.

3. The biopsy device of claim 1, further comprising a vacuum source communicating with the inner tubular cutter to prolapse tissue into the lateral tissue receiving aperture, the graphical display further operably configured to depict a mode of operation corresponding to the vacuum source.

4. The biopsy device of claim 3, further comprising a mode control and control circuitry responsive to user activation of the mode control to toggle between a plurality of modes of operation, the graphical display including a plurality of indicators illuminated to correspond to a current mode of operation.

5. The biopsy device of claim 4, further comprising a plurality of graphical depictions illustrating each of the plurality of modes of operation.

6. The biopsy device of claim 3, further comprising a lateral lumen attached to the outer cannula and communicating distally to the lateral tissue receiving aperture and proximally to atmosphere.

7. The biopsy device of claim 1, further comprising:
    a probe assembly portion containing the inner tubular cutter, a cutter carriage attached to the inner tubular cutter, and a translation shaft engaged for longitudinal translation to the cutter carriage; and
    a holster assembly including a rotation member engageable to the translation shaft.

8. The biopsy device of claim 7, wherein the probe assembly further comprises a cutter gear proximally attached to the inner tubular cutter, a rotation shaft having a spur gear portion positioned to engage the cutter gear to impart a rotation to the inner tubular cutter.

9. The biopsy device of claim 8, wherein the holster further comprises a fixed ratio transmission having one rotation output engageable to the translation shaft and another rotation output engageable to the rotation shaft.

10. The biopsy device of claim 9, further comprising a remotely positioned cutter translation motor coupled via a mechanical drive cable attached to the holster.

11. The biopsy device of claim 10, wherein the mechanical drive cable is attached to an undersurface of the holster to reduce torque loads at the outer cannula.

12. The biopsy device of claim 8, wherein the spur gear portion is longitudinally dimensioned to disengage from the cutter gear when all of the inner tubular cutter is retracted proximally to the lateral tissue receiving aperture.

13. The biopsy device of claim 1, further comprising a sensor associated with the cutter.

14. The biopsy device of claim 13, wherein the sensor is responsive to translation of the cutter, wherein the graphical display is responsive to the sensor to depict translation of the cutter.

15. The biopsy device of claim 14, wherein the sensor comprises an encoder coupled with the tubular cutter.

16. A biopsy device comprising:
(a) a probe comprising:
(i) a cannula having a lateral tissue receiving aperture, and
(ii) a cutter movable relative to the cannula; and
(b) a holster in communication with the probe assembly, wherein the holster comprises a graphical feature comprising:
(i) a first indicator configured to depict a device status indicator, and
(ii) a second indicator configured to depict positioning of the cutter relative to the cannula.

17. The biopsy device of claim 16, wherein the second indicator comprises a plurality of discrete lights, wherein the second indicator is configured to selectively operate particular lights of the plurality of discrete lights based on the position of the cutter relative to the lateral tissue receiving aperture, wherein the plurality of discrete lights are in a linear arrangement.

18. The biopsy device of claim 16, wherein the second indicator is configured to depict positioning of the cutter relative to the lateral tissue receiving aperture of the cannula.

19. The biopsy device of claim 18, wherein the device status indicator is configured to illuminate in response to the biopsy device being in a selected mode of a plurality of available modes, wherein the second indicator is configured to depict positioning of the cutter relative to the lateral tissue receiving aperture for each selected mode of the plurality of available modes.

20. A biopsy device comprising:
(a) a handpiece including a cannula and a cutter, wherein the cutter is movable relative to the cannula, wherein the cannula includes a lateral port for receiving tissue;
(b) a control unit operatively associated with the handpiece; and
(c) a graphical feature associated with the handpiece, wherein the graphical feature is in communication with the control unit, wherein the graphical feature includes a plurality of indicators, wherein each indicator of the plurality of indicators is responsive to the control unit to indicate an operational status of the biopsy device.

* * * * *